US008975395B2

(12) United States Patent
Meyer et al.

(10) Patent No.: US 8,975,395 B2
(45) Date of Patent: Mar. 10, 2015

(54) MATERIALS FOR THE SOLID/LIQUID EXTRACTION OF HEAVY METAL IONS, CONTAINING SUPPORTED N-FUNCTIONALIZED POLYAZACYCLOALKANES

(75) Inventors: Michel Meyer, Dijon (FR); Arnaud Bucaille, Colombes (FR); Francois Cuenot, Issy-les-Moulineaux (FR); Franck Denat, Dijon (FR); Frédéric Boschetti, Dijon (FR); Roger Guilard, Fontaine-les-Dijon (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 924 days.

(21) Appl. No.: 12/735,980

(22) PCT Filed: Feb. 20, 2009

(86) PCT No.: PCT/FR2009/050271
§ 371 (c)(1),
(2), (4) Date: Nov. 29, 2010

(87) PCT Pub. No.: WO2009/112736
PCT Pub. Date: Sep. 17, 2009

(65) Prior Publication Data
US 2011/0079557 A1  Apr. 7, 2011

(30) Foreign Application Priority Data
Feb. 28, 2008  (FR) ...................... 08 51306

(51) Int. Cl.
*C07D 257/02* (2006.01)
*B01J 20/22* (2006.01)
*B01J 20/26* (2006.01)
*C07F 7/08* (2006.01)

(52) U.S. Cl.
CPC ........... *C07F 7/0836* (2013.01); *C07B 2200/11* (2013.01)
USPC ............ 540/474; 502/401; 502/402

(58) Field of Classification Search
USPC .......... 540/553, 554, 609, 610; 502/400, 401, 502/402
See application file for complete search history.

(56) References Cited

U.S. PATENT DOCUMENTS 6,174,505 B1  1/2001  Guilard et al.
6,524,372 B1 *  2/2003  Corriu et al. .................... 95/138

FOREIGN PATENT DOCUMENTS

EP       1 218 104          10/2006
WO    WO 01/46202     *  6/2001 ............... C07F 7/18
WO    WO 03/029228         4/2003

OTHER PUBLICATIONS

Corriu, R.J.P. et al., "Coordination Chemistry in the Solid: Evidence for Coordination Modes within Hybrid Materials Different from those in Solution." Chem. Eur. J. (2002), vol. 8, No. 24, pp. 5732-5741.*
Brandes et al., "De la molecule au procede: Apports des materiaux hybrides organiques-inorganiques en chimie separative." L'actualite chimique (Oct.-Nov. 2005), vol. 290-291, pp. 108-117 (in French, with Google Translate machine translation attached).*

* cited by examiner

*Primary Examiner* — Stanley Silverman
*Assistant Examiner* — Daniel Berns
(74) *Attorney, Agent, or Firm* — Jacobson Holman PLLC

(57) ABSTRACT

The present invention relates to a material notably adapted for the extraction of metal cations in an aqueous medium, comprising a solid support on which are attached polyazacycloalkane compounds having a ring including at least 4 nitrogen atoms, and wherein the nitrogen atoms of the ring are substituted with coordinating groups, which each are independently:

a coordinating group of formula:

—$(CH_2)_n$—C(=O)—$NR^1R^2$ or else
a both coordinating and binding group, fitting the formula:

—$(CH_2)_p$—C(=O)—$NR^3$-(A)-[support].

The invention also relates to methods for preparing the aforementioned materials and to different uses thereof, notably for the extraction of $Pb^{2+}$ cations in an aqueous medium.

15 Claims, No Drawings

MATERIALS FOR THE SOLID/LIQUID EXTRACTION OF HEAVY METAL IONS, CONTAINING SUPPORTED N-FUNCTIONALIZED POLYAZACYCLOALKANES

This is a 371 of PCT/FR09/050271 filed Feb. 20, 2009, which has a priority of French no. 08 51309 filed Feb. 28, 2008, hereby incorporated by reference.

The present invention relates to the field of solid/liquid extraction of metal cations, and notably of heavy metal cations (in particular lead, cadmium, copper or nickel cations) present in liquid media. The invention more specifically relates to the solid materials designed hereafter under the generic term of "extraction materials", which allow trapping of metal cations in a liquid medium and their extraction out of such a liquid medium, and which i.a. prove to be particularly well adapted to the extraction of $Pb^{2+}$ cations out of aqueous media. The invention also relates to methods for synthesizing such extracting materials.

The solid/liquid extraction of heavy metal cations out of liquid media, notably out of aqueous media, is a well-known technique, to which it is often resorted industrially. As a general rule, such a solid/liquid extraction is conducted by putting the liquid medium to be treated, contaminated by heavy metal cations, in contact with a solid capable of complexing these heavy metal cations, whereby at least one portion of the heavy metal cations present in the liquid medium are found trapped by the solid, thereby inducing purification of the liquid medium. Extraction techniques of this type find many practical applications, among which may notably be mentioned the treatment of drinking water before its consumption, or else further the treatment of waste water or industrial effluents (notably aqueous effluents) before their being discharged into the environment.

Many extraction techniques of the aforementioned type have been developed and used for a long time. Within this scope, the use of ion exchange resins has notably been described, capable of binding certain metal cations, such as for example the chelating resin Amberlyst IRC718® marketed by Rohm & Haas which includes iminidiacetate groups giving it good affinity for copper and iron cations, or else the GT73® resin based on a polystyrene matrix modified by sulfur-containing end groups, which is itself adapted to scavenging copper, silver, cadmium and lead.

More generally, the use of functionalized polymers has been contemplated, for example of the type of polymeric beads bearing dithiocarbamate groups described in *Polyhedron*, Vol. 15, pp. 4241-4254 (1996) or scavenging materials based on polymers bearing acrylic end groups of the type of those disclosed in *Energy Fuels*, Vol. 12, pp. 792-797 (1998). It is also known that certain natural materials such as lignin or chitosan have the property of binding certain heavy metals, this capability may further be improved by grafting sequestering groups on this type of materials. On this subject, it is notably possible to refer to *Water Res.*, Vol. 33, pp. 2469-2479 (1999) or to *Bull. Chem. Soc. Jpn*, Vol. 70, pp. 2446-2447 (1997).

Moreover extracting materials have been proposed based on an inorganic support, among which mention may be made of absorbance of cations based on immobilized ligands on silica gels or mesoporous silicas, of the type of those described for example in *Chem. Commun.* pp. 258-259 (2000), *J. Chem. Soc, Dalton Trans.*, pp. 2206-2209 (2001), *Science*, Vol. 276, pp. 923-926 (1997) or Adv. Mater., Vol. 9, pp. 550-503 (1997).

More generally, a large number of methods have been described relying on the surface modification of organic or mineral supports by groups coordinating, complexing or sequestering metal cations, the extraction of which is sought. In the sense of the present description, such coordinating, complexing or sequestering groups will be designated by the generic term of "coordinating group".

Notably taking into account increasingly strict statutory requirements in terms of public health and discharges into the environment, there is today a real need for solid/liquid extraction methods allowing particularly efficient and selective removal of metal cations of the heavy metal cation type within liquid media. Such methods are most particularly required in the field of treatment of drinking waters intended for human consumption, where requirements as regards residual heavy metal contents, and notably lead content, are increasing strict.

As an indication, the standard presently in effect in France (set by the decree No. 2001-1220 as of Dec. 20, 2001 applying the European directive 98/83/EC of Nov. 3, 1998) sets at 25 micrograms per liter (i.e. 25 ppb) the maximum admissible lead content in drinking water, and this threshold will be 10 micrograms per liter (10 ppb) from Dec. 25, 2013. As regards treatment of waters intended to be consumed, there is therefore a need for extraction methods for lead and possible other heavy metals until contents as low as a few ppb are obtained, and this preferably without extracting in the same time other useful species present in drinking water, such as for example alkaline or earth alkaline cations. Methods of this type, allowing efficient extraction of heavy metals are also of interest for treating waste waters or industrial aqueous effluents, insofar that the acceptable residual heavy metal contents for effluents discharged into the environment themselves also tend to become increasingly low.

A method developed in this direction was notably described in the international application WO 01/46202, which relates to extracting materials notably intended for extracting $Pb^{2+}$ ions in an aqueous medium, which comprises a support of the silica gel type, grafted by N-functionalized polyazacycloalkanes. By using these supported N-functionalized polyazacycloalkanes, it is of course possible to attain greater purification thresholds than those obtained by using commercial ion exchanger resins, but the materials disclosed in this application however prove to be insufficient, in the most general case for obtaining an extensive purification level of the type required in the treatment of drinking water.

An object of the present invention is to provide novel solid extracting materials adapted to solid/liquid extraction of metal cations in a liquid medium notably allowing more efficient removal of $Pb^{2+}$ cations than that obtained with materials disclosed in the aforementioned WO 01/46202. More generally, the invention has the object of providing a solid extracting agent allowing extraction of lead ions and preferably ions of other heavy metals out of a liquid medium (and most particularly out of an aqueous medium) with sufficient efficiency for meeting the demands required in the field of purification of drinking waters and of treatment of industrial effluents and waste waters before their discharge in the environment.

In order to achieve these objects, according to a first aspect, the present invention provides a material adapted to the extraction of metal cations. This material comprises a solid support (designated hereafter by S) on which are bound in a covalent way polyazacycloalkane compounds (designated hereafter by PACs) having a ring including at least 4 nitrogen atoms, and wherein each of the nitrogen atoms of the ring is substituted with a coordinating group, each of the coordinating groups borne by the nitrogen atoms of the ring of a PAC bound to the support (S) being independently of each other:
either a coordinating group, designated hereafter by Rc group, fitting the following general formula:

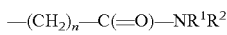

wherein:
n=1, 2 or 3;
$R^1$ and $R^2$ are identical of different and each of them represents a hydrogen atom or an alkyl radical comprising 1 to 4 carbon atoms, or an alkenyl radical comprising 1 to 4 carbon atoms or an aryl radical;
or a coordinating and binding group, designated hereafter by RcL group, fitting the following general formula:

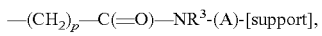

wherein:
p=1, 2 or 3;
$R^3$ represents a hydrogen atom, or an alkyl radical comprising 1 to 4 carbon atoms, or an alkenyl radical comprising 1 to 4 carbon atoms, or an aryl radical (preferably a hydrogen atom or an alkyl radical comprising 1 to 4 carbon atoms);
-(A)- represents a saturated or unsaturated linear or branched hydrocarbon chain, optionally totally or partly cyclized and optionally interrupted by one or more heteroatoms, bound by at least one covalent bond to the solid support (S).

Thus, an extracting material according to the invention is a material based on a solid support (S) modified by covalent grafting of polyazacycloalkane compounds (PACs) including 4 or more nitrogen atoms, each of these compounds (PACs) being specifically substituted with a coordinating group (Rc or RcL) as defined above on each of the nitrogen atoms of its ring.

The exact nature of the solid support (S) on which are bound the polyazacycloalkane compounds (PACs) may vary to a rather wide extent, subject to allowing covalent grafting of the compounds (PACs) on its surface as required according to the invention. According to a generally interesting, although not systematic, embodiment, it is typically possible to use as a solid support (S), a solid support comprising a mineral oxide, generally at least at its surface.

According to an embodiment which proves to be particularly interesting, the solid support (S) used according to the invention comprises silica gel. According to a specific embodiment generally well adapted to the application of the invention, the support (S) used is formed by such a silica gel. Silica gels useful as a support (S) according to the present invention, are notably amorphous silica gels of the Kieselgel type or mesostructured silica gels of the MTS type notably described in *J. Chem. Soc, Dalton Trans.*, pp. 1209-1214 (1996) and *Chem. Mater.*, Vol. 13, pp. 3151-3168 (2001).

In the sense of the present description, the expression "polyazacycloalkane compound" designates an organic compound including a polyazacycloalkane ring, i.e. a saturated ring of the polyazacycloalkane type where several of the groups ($CH_2$) are replaced with secondary or tertiary amine functions (in other words, a polyazacycloalkane ring is a cycloalkane chain interrupted by several nitrogen atoms).

The polyazacycloalkane compounds used within the scope de la present invention systematically have a ring comprising at least 4 nitrogen atoms, and this number of nitrogen atom most often remains less than or equal to 12, and more preferably less than 8 (typically, this number of nitrogen atoms is equal to 4, 5 or 6).

The polyazacycloalkane ring of the polyazacycloalkane compounds (PACs) present on the extracting materials of the present invention is typically a cyclic link of 4 to 12 (post often 4 to 8, for example 4, 5 or 6) identical or different units of formula $-N(CH_2)_n-$, wherein, in each of said units, n designates independently an integer comprised between 1 and 4, and more preferably an integer equal to 2 or 3.

According to an advantageous embodiment of the present invention, the polyazacycloalkane compounds (PACs) present on the extracting material of the present invention are at least partly (and preferably totally) tetraazacycloalkane compounds, i.e. compounds bearing a ring exactly including 4 nitrogen atoms, this ring being preferably:

a 1,4,8,11-tetraazacyclotetradecane ring with 14 links, fitting the following formula:

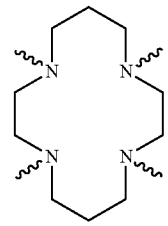

or else a 1,4,7,10-tetraazacyclotridecane ring with 13 links, having the formula below:

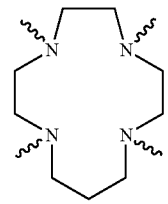

Whatever its correct nature, the polyazacycloalkane ring of polyazacycloalkane compounds (PACs) present on an extracting material according to the invention is systematically functionalized by an Rc or RcL group of the aforementioned type on each of the nitrogen atoms of its ring. Each of these Rc and Rcl groups, which have the capacity of being able to complex metal cations, is designated herein by the generic term of "coordinating group". The presence of such a group with coordinating nature at each of the nitrogen atoms of the ring of the polyazacycloalkane compounds (PACs) is a specificity of the materials of the invention which is made possible by the specific preparation method developed for this purpose within the scope of the present invention and which is described in the present description later on.

The work carried out by the inventors within the scope of the present invention has now allowed a demonstration that the systematic presence of coordinating groups on each of the nitrogen atoms of the polyazacycloalkane ring gives to the materials of the invention very high extraction efficiency for certain metal cations, in particular heavy ion cations such as $Pb^{2+}$, $Cd^{2+}$, $Cu^{2+}$, $Zn^{2+}$ or $Ni^{2+}$. The materials of the invention prove to be most particularly well adapted for isolating or removing these cations in different liquid media, and notably in aqueous media, and this both in a static mode and in a dynamic mode.

In particular, the materials of the invention prove to be most particularly adapted to treatment of drinking water. They notably allow very efficient removal of $Pb^{2+}$ cations, which proves to be suitable for rather easily reaching the required purification level in the field of drinking water. The work of the inventors more specifically gives the possibility of establishing that the materials of the invention are capable of ensuring extremely efficient decontamination of an aqueous medium contaminated by lead, by finally obtaining without any difficulty residual lead contents of less than 10 micrograms per liter, and this while having the advantage of not retaining alkaline and earth alkaline cations at the same time. Such a performance level may further be obtained, including in a dynamic mode, which opens the possibility of efficiently using the extracting materials of the invention in purifying cartridges for drinking water simply placed upstream or downstream from a domestic tap for distributing drinking water. Thus, for example, the work of the inventors has notably shown that an extracting material according to the invention may be efficiently used in order to reduce the concentration of $Pb^{2+}$ cations to a residual content of the order of 10 ppb or less for drinkable water conveyed by a lead pipe, and this simply by means of a suitable purifying cartridge placed at the outlet of the water distribution tap (for example a cartridge of the type described in patent JP 02 301469).

Without intending to be bound to a particular theory, the work carried out by the inventors gives the possibility of putting forward that the excellent extraction capacities obtained within the scope of the invention seem to be due to the fact that the polyazacycloalkane compounds immobilized on the support (S) have a capacity of complexing metal cations substantially similar to the one they would have if they were in the free state within a liquid medium. In fact, it seems that considering the specific presence of a coordinating group at each of the nitrogen atoms of their ring, the polyazacycloalkane compounds immobilized on the support (S) behave like "molecular claws" capable of efficiently chelating cations of suitable size, schematically in the same way as the same compounds present in the free state within a liquid medium.

In other words, the extracting materials of the invention may, somewhat, be described as an immobilized form of complexing agents of the polyazacycloalkane type having not lost their complexing efficiency because of their covalent grafting on a solid support. It should be noted that the materials of the invention thereby constitute a significant advance as compared with the polyazacycloalkane compounds immobilized on a support, described in the aforementioned application WO 01/46202, for which covalent grafting systematically requires immobilization of at least one of the nitrogen atoms of the polyazacycloalkane ring, and which are therefore in fine again found without at least one coordinating group, thereby reducing the efficiency of the "molecular claw" ensured by the coordinating groups capable of being borne by the nitrogen atoms of the polyazacycloalkane group.

Notably, in order to obtain the highest possible efficiency for complexing metal cations for a material according to the invention, most often it proves to be preferable to select polyazacycloalkane compounds wherein the coordinating groups remain as free as possible to ensure their role of molecular claw able to immobilize a metal cation. For this purpose, it is generally preferable to limit the number of coordinating groups of polyazacycloalkane compounds which are found again immobilized on the support (S), which, if they were in a too large number, would be capable of leading to stiffening of the ring, potentially detrimental to the efficiency of complexation of the cations.

In the most general case, it notably proves to be preferable that the coordinating groups borne by the nitrogen atoms of the ring of polyazacycloalkane compounds (PACs) comprise the less possible number of RcL groups (coordinating and binding groups) fitting the aforementioned formula $-(CH_2)_p-(=O)-NR^3-(A)$-[support]. According to a particularly interesting embodiment, the coordinating groups formed by the nitrogen atoms of the ring of polyazacycloalkane compounds (PACs) comprise at most a coordinating and binding group RcL of this type.

According to a first interesting alternative, an extracting material according to the invention may advantageously comprise polyazacycloalkane compounds (PACs) immobilized on the solid support (S) without any coordinating group bound to the support, i.e. polyazacycloalkane compounds only bearing coordinating groups Rc excluding any RcL group.

According to this first alternative of the invention, the extracting material preferably comprises polyazacycloalkane compounds (PACs) immobilized on the solid support (S), which fit the following formula (I):

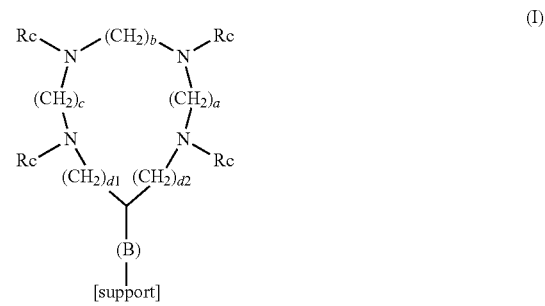

wherein:
- a, b and c are three integers, either identical or different, each of a, b and c being equal to 2 or 3;
- d1 and d2 are two integers, either identical or different, equal to 0, 1 or 2, it being understood that the sum (d1+d2) has the value 1 or 2;
- each of the 4 Rc groups, either identical or different (and most often identical) represent a group fitting the general formula:

$-(CH_2)_n-C(=O)-NR^1R^2$ as defined above;
- —(B)— is a saturated or unsaturated linear or branched hydrocarbon chain, optionally totally or partly cyclized, and optionally interrupted by one or more heteroatoms, bound by at least one covalent bond to the solid support (S).

According to this first alternative, it often proves to be advantageous that all the polyazacycloalkane compounds (PACs) immobilized on the solid support (S) fit the aforementioned formula (I).

Polyazacycloalkane compounds particularly well adapted to the application of the first alternative of the invention are compounds fitting the formula (I) given above. Moreover, in the compounds of formula (I), it often proves to be interesting that b=3 and (d1+d2)=2, and in that in particular when a=c=2 (the case when b=2 and (d1+d2)=2 and the case when b=3 and (d1+d2)=1 may also be considered, in particular when a=c=2, but they often prove to be less interesting).

An extracting material according to the first alternative of the invention which generally proves to be particularly suitable as an extracting material, comprises polyazacycloalkane compounds (PACs) immobilized on the solid support (S) fitting the following formula (Ia) (preferably excluding any other polyazacycloalkane compound):

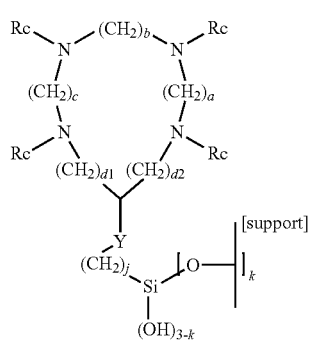

(Ia)

wherein:
- a, b, c, d1, d2, as well as the groups Rc have the meanings given above for formula (I);
- —Y— is a saturated or unsaturated linear or branched divalent hydrocarbon group, optionally totally or partly cyclized and optionally interrupted by one or more heteroatoms;
- j is an integer equal to 0, 1, 2 or 3; and
- k, which represents the number of bonds between the cyclic species and the solid support (S), is an integer equal to 1, 2 or 3.

According to a particular embodiment of the first alternative of the invention, the polyazacycloalkane compounds (PAC) immobilized on the solid support (S) fit one of the formulae below:

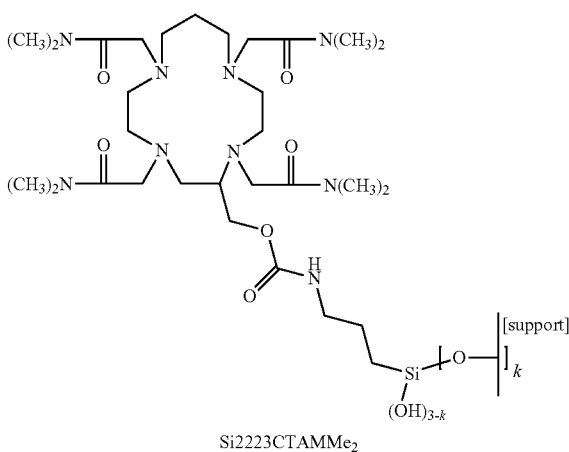

Si2223CTAMMe$_2$

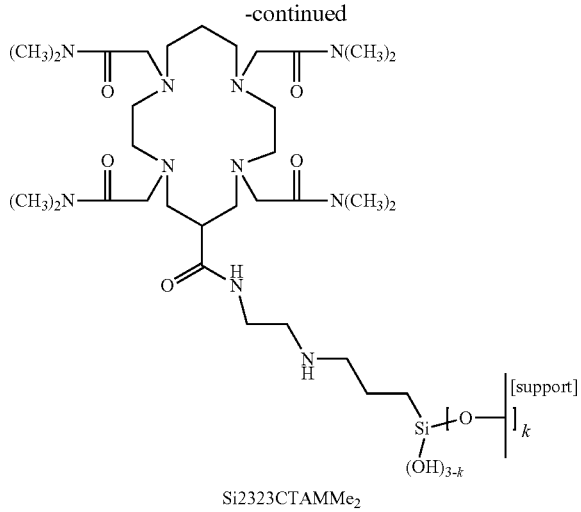

Si2323CTAMMe$_2$ wherein k has the aforementioned definition.

According to a second interesting alternative, other than the alternative defined above, an extracting material according to the invention may comprise polyazacycloalkane compounds (PACs) immobilized on the solid support (S) via a bond ensured by a both coordinating and binding group RcL of the aforementioned type. In this particular scenario, it is often preferable that each of the thereby immobilized polyazacycloalkane compounds only comprises a single RcL group and that the whole of the other coordinating groups are non-binding coordinating groups Rc.

According to this second alternative of the invention, the extracting material of the invention preferably comprises polyazacycloalkane compounds (PACs) immobilized on the solid support (S) which fit the following formula (II):

$$\text{(II)}$$

wherein:
- a, b, c and d are three integers, either identical or different, each of a, b, c and d being equal to 2 or 3;
- each of the 3 Rc groups, either identical or different (and most often identical) represents a group fitting the general formula:

—(CH$_2$)$_n$—C(=O)—NR$^1$R$^2$ having the aforementioned definition; and
- p, R$^3$ and -(A)- have the aforementioned definitions.

It often proves to be advantageous, within the scope of this second alternative, that all the polyazacycloalkane compounds (PACs) immobilized on the solid support (S) fit the aforementioned formula (II).

Polyazacycloalkane compounds particularly well adapted to applying the second alternative of the invention are compounds fitting the formula (II) given above, wherein a=c=2. Moreover, in the compounds of formula (II), it often proves to be preferable that b=d=3, and this quite notably when a=c=2 (the case of b=3 and d=2 and the case of b=2 and d=3 may also be considered, notably when a=c=2, but often they do prove to be less interesting).

An extracting material according to the second alternative of the invention which generally proves to be particularly well adapted as an extracting material comprises polyazacycloalkane compounds (PACs) immobilized on the solid support (S) fitting the following formula (IIa) (preferably excluding any other polyazacycloalkane compound):

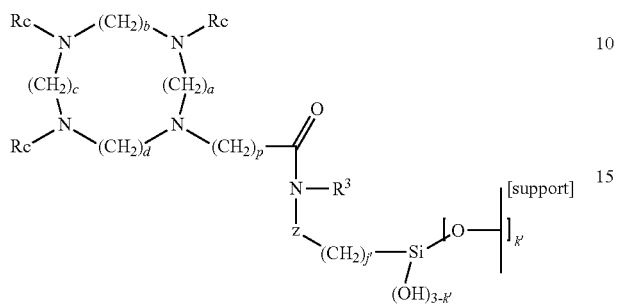

(IIa)

wherein:

a, b, c, d, p and the groups Rc and $R^3$ have the meanings given above for formula (II);

z is a saturated or unsaturated, linear or branched divalent hydrocarbon group, optionally totally or partly cyclized (for example as an aryl group) and optionally interrupted by one or more heteroatoms (z may for example a divalent alkylene group containing 1 to 8 carbon atoms, for example 2, 3, 4 or 5 carbon atoms). According to a specific embodiment, z may comprise a carbonyl group (for example included in a urea group);

j' is a integer equal to 0, 1, 2 or 3; and k', which represents the number of bonds in the cyclic species and the solid support (S), is an integer equal to 1, 2 or 3.

According to a particular embodiment of the second alternative of the invention, the polyazacycloalkane compounds (PACs) immobilized on the solid support (S) fit one of the formulae below:

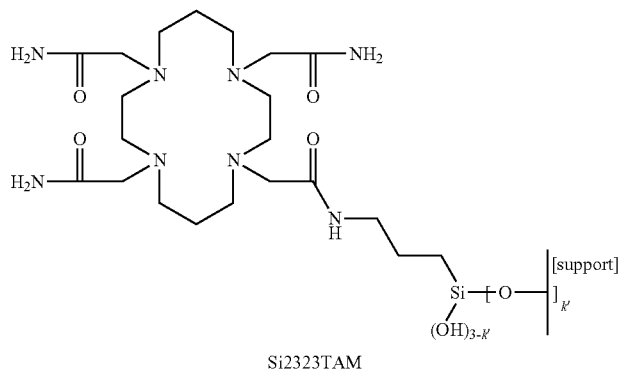

Si2323TAM

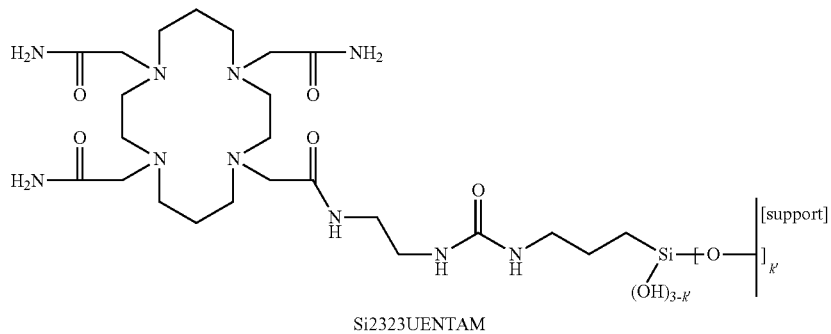

Si2323UENTAM

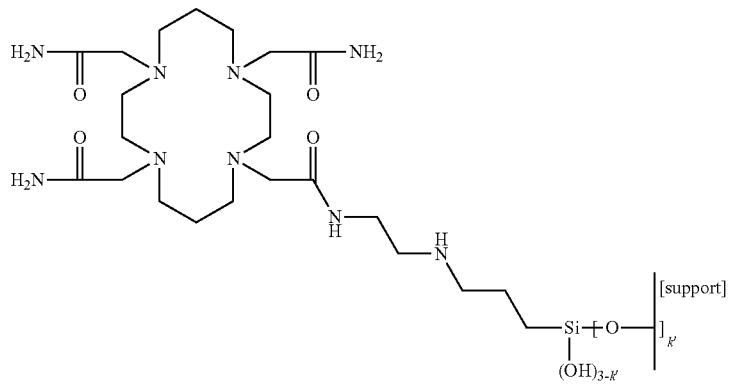

Si2323ENTAM

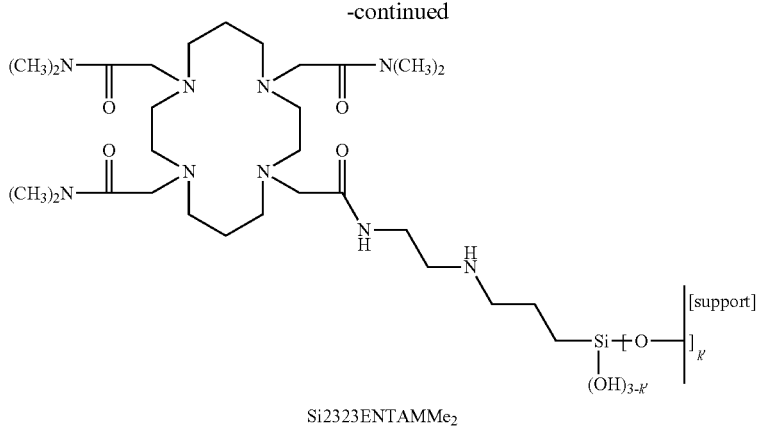

Si2323ENTAMMe₂ wherein k' is as defined above.

According to a particular aspect, the object of the present invention is a method giving access to extracting materials as defined above. This method for preparing materials of the invention generally includes the steps hereafter:

(E1) a solid support is provided including at the surface, functions Fs capable of reacting with complementary functions, said Fc functions, in order to form a chemical covalent bond;

(E2) functionalized polyazacycloalkane compounds (PAC$^f$) bearing an Fc function of the aforementioned type are prepared from polyazacycloalkane compounds (PAC$^0$) having a ring including at least 4 nitrogen atoms,
by attaching (in one or several steps) a coordinating functional group on each of the nitrogen atoms of the ring of the polyazacycloalkane compounds (PAC$^0$),
wherein each of said coordinating functional groups attached on the nitrogen atoms of the ring is, independently of the others:
a coordinating group Rc fitting the general formula:

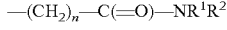
—(CH$_2$)$_n$—C(=O)—NR$^1$R$^2$ wherein n, R$^1$ and R$^2$ have the aforementioned meanings;
or
a coordinating and reactive group RCr fitting the following general formula:

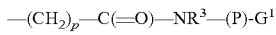
—(CH$_2$)$_p$—C(=O)—NR$^3$—(P)-G$^1$ wherein:
p and R$^3$ have the aforementioned meanings;
—(P)— represents a chemical bond or else a saturated or unsaturated, linear or branched hydrocarbon chain, optionally totally or partly cyclized (for example as an aryl group) and optionally interrupted by one or more heteroatoms, bound through at least one covalent bond to the solid support (S); and
-G$^1$ is a functional group bearing a function Fc capable of reacting with the functions Fs borne by the solid support, provided in step (E1) for forming a covalent bond between the polyazacycloalkanes (PAC$^f$)
it being understood that, in the case when none of the functional groups attached on the nitrogen atoms of the ring is a group Rcr, then the polyazacycloalkanes (PAC$^f$) are further functionalized on one of the carbon atoms of the ring by a reactive group Rr of general formula -(Q)-G$^2$, wherein:
-(Q)- represents a chemical bond or else a saturated or unsaturated, linear or branched hydrocarbon chain, optionally totally or partly cyclized (for example as an aryl group) and optionally interrupted by one or more heteroatoms, bound through at least one covalent bond to the solid support (S); and
-G$^2$ is a functional group bearing an Fc function capable of reacting with the Fs functions borne by the solid support provided in step (E1) for forming a covalent bond between the polyazacycloalkanes (PAC$^f$), and (E3) the functionalized polyazacycloalkanes (PAC$^f$) obtained in step (E2) are put into contact with the solid support provided in step (E1).

The method of the invention applying the steps (E1), (E2) and (E3) above specifically applies the reaction of Fs functions borne by the solid support provided in step (E1) with complementary Fc functions borne by the functionalized polyazacycloalkanes (PAC$^f$) prepared in step (E2), these Fc functions may be borne by an Rcr group or by an Rc group introduced in step (E2).

The Fs functions borne by the support may be functions inherent to said support (for example —OH functions when the support is a mineral oxide such as silica gel) or else functions grafted on said support (functions of the type —Cl or —NH$_2$ for example), the step (E1) then comprising a preliminary step for functionalizing this support with Fs groups.

Not as a limitation, the Fs functions borne by the solid support provided in step (E1) and the complementary functions Fc borne by the functionalized polyazacycloalkanes (PAC$^f$) obtained in the step (E2) may for example be selected from the pairs of functions Fs/Fc below:
Fs=—OH/Fc=—Si(OR)$_3$ wherein R is an alkyl group comprising 1 to 4 carbon atoms (typically 1 or 2);
Fs=—X/Fc=—NH$_2$ wherein X is a halogen atom (preferably Cl);
Fs=—Si—H/Fc=—CH$_2$—CH=CH$_2$;
Fs=—Si—H/Fc=-Ph-CH=CH$_2$ wherein Ph represents an aromatic ring either substituted or not (for example a benzene ring, either substituted or not).

An important specificity of the method of the invention is that step (E2) is specifically conducted so that the polyazacycloalkane compounds (PAC$^f$) are functionalized by attaching a coordinating functional group on each of the nitrogen atoms of the ring of the polyazacycloalkane compounds (PAC⁰). This is ensured in step (E2) by functionalizing each of the nitrogen atoms of the polyazacycloalkane ring with an Rc or Rcr group of the aforementioned type.

Generally it is preferred that step (E2) be conducted by attaching as less as possible coordinating and reactive functional groups of the Rcr type, whereby in fine a material is obtained wherein the polyazacycloalkanes are bearers of a reduced number of coordinating and binding groups of the RcL type, as defined above in the present description. Thus, according an interesting embodiment of the method of the invention, it is preferred that at most one of the coordinating functional groups attached in step (E2) be a coordinating and reactive group of the Rcr type of the aforementioned type, whereby in the synthesized material the coordinating groups borne by the nitrogen atoms of the ring of the polyazacycloalkane compounds (PACs) comprise at most one coordinating and binding group RcL.

Generally, when in step (E2) a coordinating group or a coordinating and reactive group Rcr are attached on one of the nitrogen atoms of the ring of the polyazacycloalkane compounds (PAC⁰), this group may be grafted in a single or in several steps. Moreover, an Rcr group may be obtained by modifying a group of Rc type grafted beforehand. Thus, according to a particular embodiment, the step (E2) of the method of the invention may typically be conducted by grafting (in one or several steps) a coordinating group Rc on each of the nitrogen atoms of the ring of the polyazacycloalkane compounds (PAC⁰), and then by introducing an Fc function on the thereby obtained modified polyazacycloalkane compounds, this introduction may be carried out either by grafting a group Rc on the ring and/or by converting one or more of the Rc groups into Rcr groups (this conversion of an Rc group into an Rcr one is performed by functionalizing said group Rc with an Fc function).

According to a particular embodiment adapted for preparing extracting materials according to the first alternative of the invention, wherein the polyazacycloalkane compounds (PACs) do not contain any RcL group, the step (E2) may for example be conducted as follows:
  a coordinating group Rc as defined earlier is attached (in one or more steps) on each of the nitrogen atoms of the ring of the polyazacycloalkane compounds (PAC⁰); and, a priori or a posteriori,
  the polyazacycloalkanes (PACᶠ) are further functionalized on one of the carbon atoms of the ring with a reactive group Rr of formula -(Q)-G² as defined above.

When the method of the invention is intended to provide extracting materials bearing polyazacycloalkanes of formula (I) according to the first alternative of the invention, the polyazacycloalkane compounds (PACᶠ) prepared in step (E2) advantageously fit the following general formula (If):

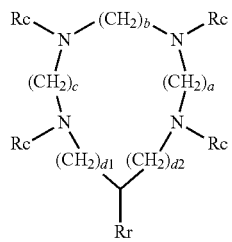

wherein:
  a, b, c, d1, d2 and Rc have the definitions given above for formula (I); and
  Rr is a reactive group of general formula -(Q)-G² having the aforementioned definition.

According to a first specific embodiment with which extracting materials bearing polyazacycloalkanes of formula (Ia) according to the first alternative of the invention may be obtained, the method of the invention is conducted as follows:
  the solid support provided in step (E1) is a silica gel which includes its surface —OH functions as Fs functions; and
  the compounds (PACᶠ) prepared in step (E2) are compounds bearing trialkoxysilane functions —Si(OR)₃ as Fc functions, which fit the following general formula (If-a1):

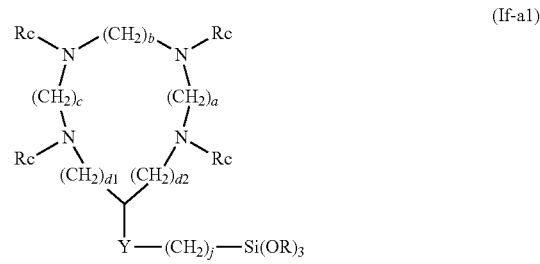

wherein:
  a, b, c, d1, d2, Rc, —Y— and j are as defined above for formula (Ia); and
  R is an alkyl group comprising 1 to 4 (typically 1 or 2) carbon atoms.

Preferably, according to this first particular embodiment, the compounds (PACᶠ) prepared in step (E2) fit the following formula (If-a1.1):

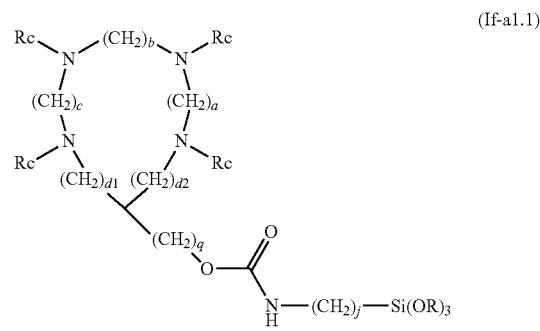

wherein:
  a, b, c, d1, d2, Rc, j and R are as defined above for formula (Ia); and
  q is an integer of value 1, 2, 3 or 4,
said compounds (If-a1.1) being obtained in step (E2) by applying the succession of the following steps:

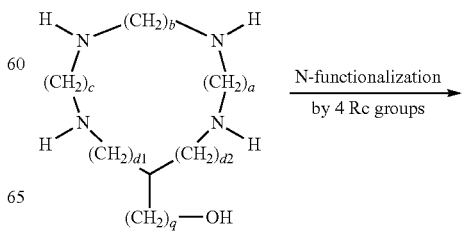

-continued

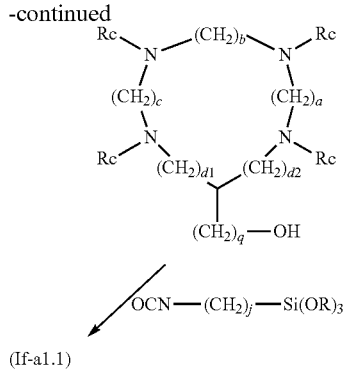

(If-a1.1)

According to a second specific embodiment with which extracting materials bearing polyazacycloalkanes of formula (Ia) according to the first alternative of the invention may be obtained, the method of the invention is conducted as follows:

the solid support provided in step (E1) is a modified silica gel which includes surface functions —X as Fs functions, wherein X is a halogen atom (preferably Cl), this modified silica gel being obtained by grafting a trialkoxysilane of formula X—$(CH_2)_j$—$Si(OR)_3$, wherein j is as defined above for formula (Ia), and R is an alkyl group comprising 1 to 4 (typically 1 or 2) carbon atoms; and the compounds ($PAC^f$) prepared in step (E2) are compounds bearing —$NH_2$ functions as Fc functions, which fit the following general formula (If-a2):

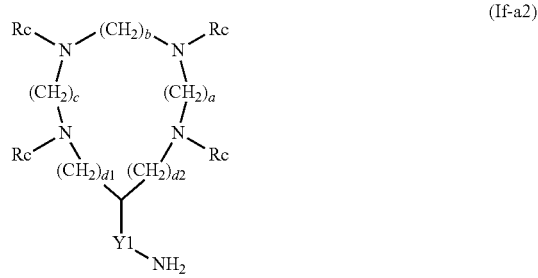

(If-a2)

wherein:
a, b, c, d1, d2, and Rc are as defined above for formula (Ia); and
-Y1- is a saturated or unsaturated, linear or branched divalent hydrocarbon group, optionally totally or partly cyclized (for example as an aryl) and optionally interrupted by one or more heteroatoms.

Preferably, according to this second particular embodiment, the compounds ($PAC^f$) prepared in step (E2) fit the following formula (If-a2.1):

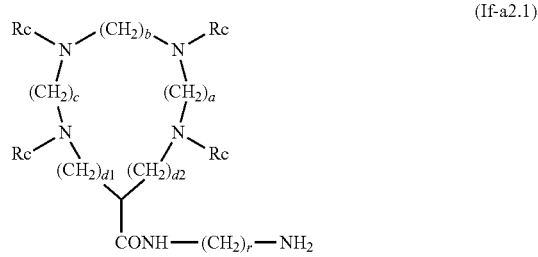

(If-a2.1)

wherein:
a, b, c, d1, d2, and Rc are as defined above for formula (Ia); and
r is an integer having the value of 1, 2, 3 or 4,
said compounds (If-a2.1) being obtained in step (E2) applying the succession of following steps:

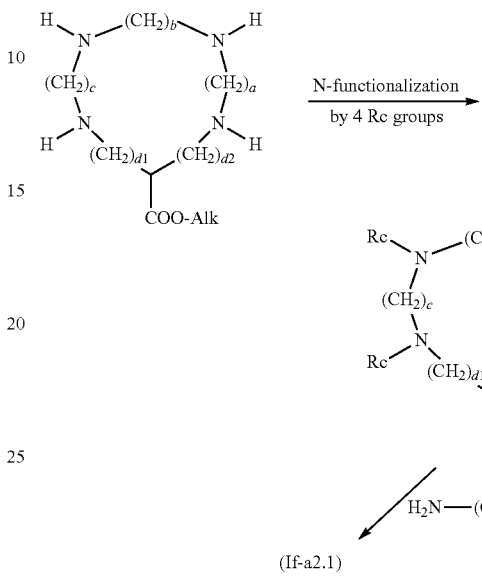

(If-a2.1)

wherein Alk is an alkyl group comprising 1 to 4 carbon atoms.

According to a particular embodiment adapted for preparing extracting materials according to the second alternative of the invention wherein the polyazacycloalkane compounds (PACs) contain a single RcL group, the step (E2) may be conducted as follows:

a reactive coordinating Rcr group is attached on one of the nitrogen atoms of the ring of the polyazacycloalkane compounds ($PAC^0$), in one or several steps;
and; a priori or a posteriori,
coordinating groups Rc are attached as defined earlier on each of the other nitrogen atoms of the ring of the polyazacycloalkane compounds ($PAC^0$), in one or several steps.

When the method of the invention is intended to provide extracting materials bearing polyazacycloalkanes of formula (II) according to the second alternative of the invention, the polyazacycloalkane compounds ($PAC^f$) prepared in step (E2) advantageously fit the following general formula (IIf):

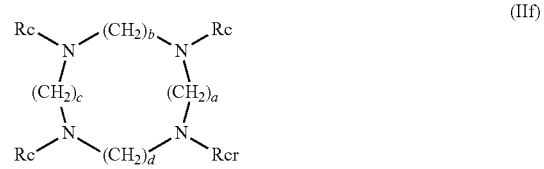

(IIf)

wherein:
a, b, c, d and Rc are as defined above for formula (II); and
Rcr is a coordinating and reactive group fitting the general formula —$(CH_2)_p$—$C(=O)$—$NR^3$—(P)-$G^1$ as defined above.

According to a first specific embodiment with which extracting materials bearing polyazacycloalkanes of formula (IIa) according to the second alternative of the invention may be obtained, the method of the invention is conducted as follows:

the solid support provided in step (E1) is silica gel, which includes its surface —OH functions as Fs functions; and the compounds (PAC$^f$) prepared in step (E2) are compounds bearing trialkoxysilane functions —Si(OR)$_3$ as Fc functions, which fit the following general formula (IIf-a1):

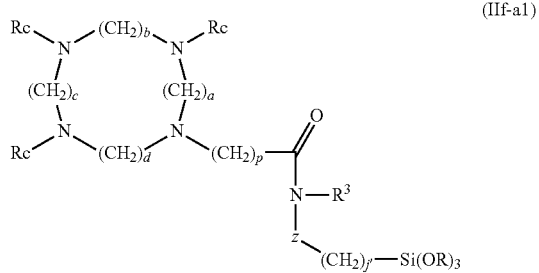

wherein:
a, b, c, d, p, Rc, R$^3$, z and j' are as defined above for formula (IIa); and
R is an alkyl group comprising 1 to 4 (typically 1 or 2) carbon atoms.

According to this first particular embodiment, in step (E2), the preparation of the aforementioned compounds (PAC$^f$) of formula (IIf-a1) may for example apply either one of the reaction schemes below:

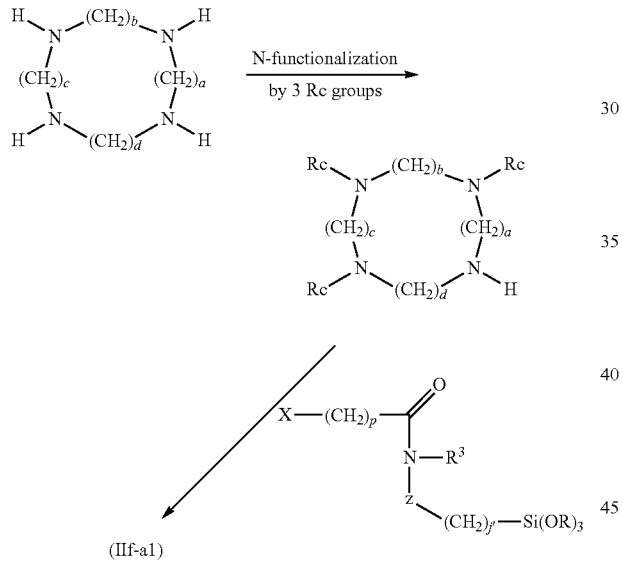

wherein X is a halogen atom, preferably Cl; or

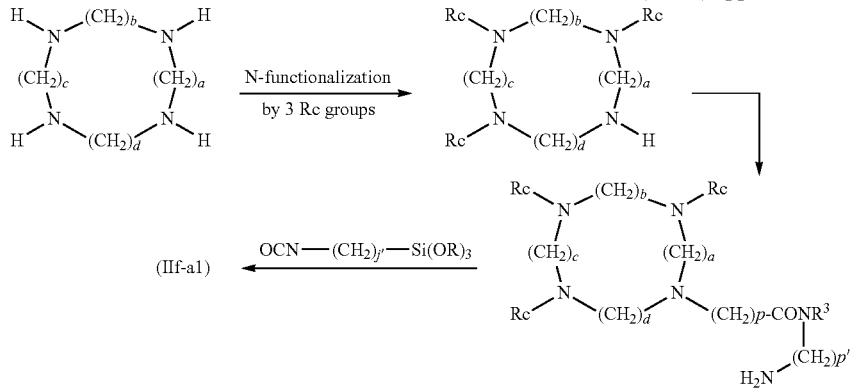

wherein p'=1, 2 or 3.

According to a second specific embodiment with which extracting materials bearing polyazacycloalkanes of formula (IIa) according to the second alternative of the invention may be obtained, the method of the invention is conducted as follows:

the solid support provided in step (E1) is a modified silica gel which includes surface —X functions as Fs functions, wherein X is a halogen atom (preferably Cl), this modified silica gel being obtained by grafting a trialkoxysilane of formula X—(CH$_2$)$_{j'}$—Si(OR)$_3$, wherein j' is as defined above for formula (IIa), and R is an alkyl group comprising 1 to 4 (typically 1 or 2) carbon atoms; and the compounds (PAC$^f$) prepared in step (E2) are compounds bearing —NH$_2$ functions as Fc functions, which fit the following general formula (IIf-a2):

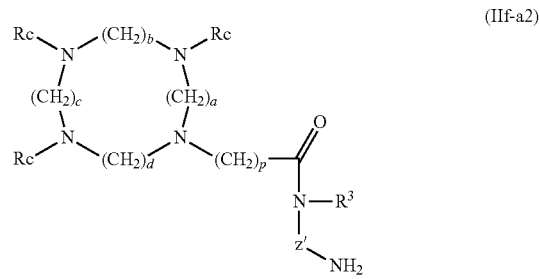

wherein:
a, b, c, d, p, Rc and R$^3$ are as defined above for formula (IIa); and
z' is a saturated or unsaturated, linear or branched, divalent hydrocarbon group, optionally totally or partly cyclized (for example as an aryl) and optionally interrupted by one or more heteroatoms, z' may typically be a divalent alkylene group containing 1 to 8 carbon atoms, for example 2, 3, 4 or 5 carbon atoms. According to a specific embodiment, z' may comprise a carbonyl group, for example included in a urea function.

Preferably, according to this particular embodiment, in step (E2), the preparation of the compounds (PAC$^f$) of formula (IIf-a2) applies the succession of following steps:

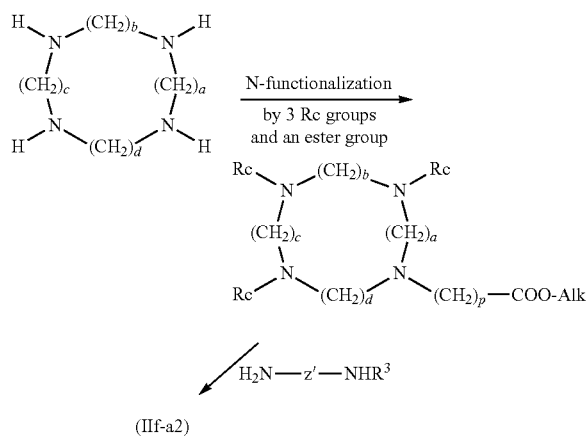

(IIf-a2)

wherein Alk is an alkyl group comprising 1 to 4 carbon atoms.

According to a third specific embodiment with which extracting materials bearing polyazacycloalkanes of formula (IIa) according to the second alternative of the invention may be obtained, the method of the invention is conducted as follows:

the solid support provided in step (E1) is a modified silica gel which includes surface —Si—H functions, this modified silica gel being obtained by grafting a trialkoxysilane of formula H—Si(OR)$_3$, wherein R is an alkyl group comprising 1 to 4 (typically 1 or 2) carbon atoms; and the compounds (PAC$^f$) prepared in step (E2) are compounds bearing —CH=CH$_2$ functions as Fc functions, which fit the following general formula (IIf-a3):

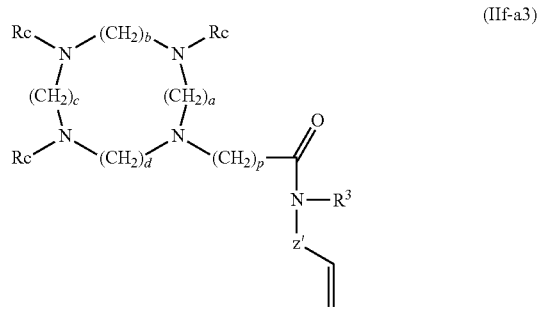

(IIf-a3)

wherein:

a, b, c, d, p, Rc, and R$^3$ are as defined above for formula (II); and

-z'- is a saturated or unsaturated linear or branched divalent hydrocarbon group optionally totally or partly cyclized and optionally interrupted by one or more heteroatoms. z' may typically be a divalent alkylene group containing 1 to 8 carbon atoms, for example 2, 3, 4 or 5 carbon atoms. According to a specific embodiment, z' may comprise a carbonyl group, for example included in a urea function.

Preferably, according to this particular embodiment, in step (E2), the preparation of the compounds (PAC$^f$) of formula (IIf-a3) applies the functionalization of the compound of the following formula:

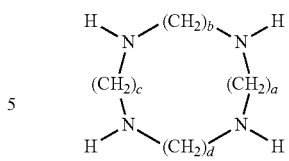

with three aforementioned either identical or different Rc groups of formula —(CH$_2$)$_p$—(C=O)—NR$^3$-z'-CH=CH$_2$. According to an embodiment which may be considered, 3 of the carbon atoms of the above tetracyclic compounds are first functionalized with three Rc groups (in one or several steps); and then the last nitrogen atom is functionalized with a —(CH$_2$)$_p$—(C=O)—NR$^3$-z'-CH=CH$_2$ group. Alternatively, conversely, one of the nitrogen atoms of the tetracyclic compound may first be functionalized with a —(CH$_2$)$_p$—(C=O)—NR$^3$-z'-CH=CH$_2$ group, and then the three other nitrogen atoms of the ring may be functionalized (in one or several steps) with three Rc groups.

According to another particular aspect, the object of the present invention is the use of the materials of the invention.

In a very general way, a material according to the invention proves to be useful for scavenging metal ions, notably Pb$^{2+}$ ions, but also Cd$^{2+}$, Cu$^{2+}$, Zn$^{2+}$, Ni$^{2+}$ cations, dissolved within a liquid medium, notably within an aqueous medium.

Within this scope, the materials of the invention may typically be applied in methods for purifying liquid media (notably aqueous media) contaminated with metal cations, wherein the medium to be treated is put into contact with an extracting material according to the invention. These methods, which may be applied according to a static or dynamic mode, are, according to a particular aspect, another object of the present invention.

A purification method applying an extracting material according to the invention proves to be particularly interesting when the liquid medium (notably an aqueous medium) subject to the purification treatment is initially contaminated with Pb$^{2+}$ cations. As indicated above in the present description, by applying extracting materials within this scope it is possible to easily attain very low lead contents in the treated medium, typically with a residual lead content of lower than 10 ppb, including when the purification method is conducted according to a dynamic mode.

The purification method of the invention may advantageously be applied to a treatment for purifying drinking water, for example by using the extracting material of the invention in a purifying cartridge placed upstream or downstream from a domestic drinking water distribution tap.

The purification method of the invention also finds interesting use for treating industrial liquid effluents (notably aqueous effluents) or waste waters.

Different aspects and advantages of the invention will furthermore become apparent in view of the illustrative examples discussed hereafter.

EXAMPLE 1

Preparation of the Material Si2323TAM (Direct Condensation of a Macrocyclic Precursor Bearing a Silane Group on Silica Gel)

In this example, a material of formula Si2323TAM as defined above in the present description was prepared according to the reaction scheme hereafter:

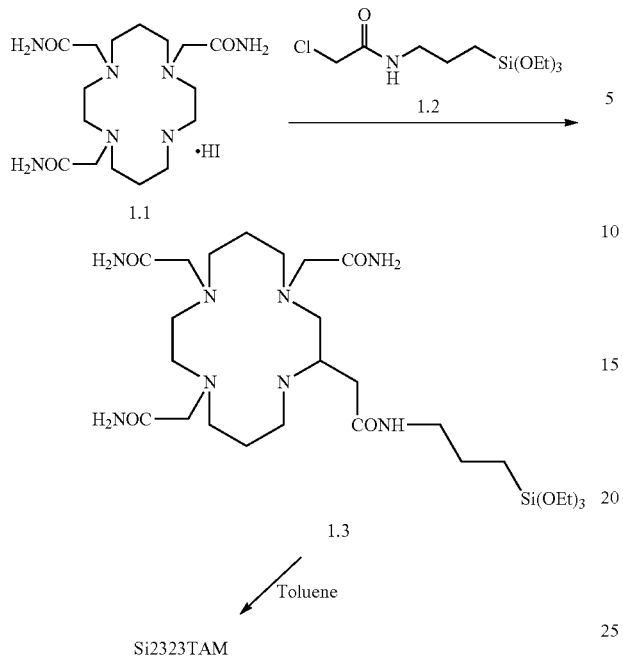

More specifically, the procedure hereafter was applied:

Preparation of Compound 1.1 (TE3AM.HI)

This compound is obtained according to the operating procedure described in *Tetrahedron Lett.*, Vol. 40, pp. 381-382 (1999).

Preparation of Compound 1.2
(N-propyltriethoxysilyl-2-chloroacetamide)

Under a nitrogen atmosphere, 75 g (540 mmol) of potassium carbonate and 21.5 mL (270 mmol) of chloroacetyl chloride are introduced in 200 mL of tetrahydrofurane. The mixture is cooled to 0° C.

To the cooled mixture are added 60 g (270 mmol) of aminopropyltriethoxysilane, dissolved in 30 mL of tetrahydrofurane, within 15 minutes by means of an isobaric dropping funnel. Stirring is maintained at room temperature of 18 h and then the reaction medium is filtered on celite.

After removing in vacuo the solvent contained in the filtrate, 46.4 g of the compound 1.2 was obtained as a pale yellow oil (yield=57%) having the NMR characteristics hereafter:

$^1$H NMR (200 MHz, CDCl$_3$): 0.60 (t, 2H, $^3$J=7.4 Hz, C$\underline{H}_2$Si); 1.20 (t, 9H, $^3$J=6.0 Hz, OCH$_2$C$\underline{H}_3$); 1.65 (p, 2H, $^3$J=7.4 Hz, CONHCH$_2$C$\underline{H}_2$); 3.25 (q, 2H, $^3$J=7.4 Hz, CONHC$\underline{H}_2$); 3.80 (q, 6H, $^3$J=6.0 Hz, OC$\underline{H}_2$CH$_3$); 4.00 (s, 2H, ClC$\underline{H}_2$); 6.77+8.25 (m, 1H, CON$\underline{H}$ cis+trans).

$^{13}$C NMR (50 MHz, CDCl$_3$): 7.9 ($\underline{C}$H$_2$Si); 18.6 (OCH$_2$$\underline{C}$H$_3$); 23.0 (NHCH$_2$$\underline{C}$H$_2$); 42.3 (NH$\underline{C}$H$_2$); 42.9 (Cl$\underline{C}$H$_2$); 58.7 (O$\underline{C}$H$_2$CH$_3$); 166.2 ($\underline{C}$O).

Preparation of the Precursor 1.3

Under a nitrogen atmosphere, 39.5 g (79 mmol) of TE3AM.HI (compound 1.1), 23.5 g (79 mmol) of the compound 1.2 and 27.4 g (200 mmol) of potassium carbonate are mixed with 800 mL of freshly distilled acetonitrile. The obtained suspension is refluxed with the solvent for 44 h. The solvent is then evaporated. The obtained compound is solubilized in 1 L of chloroform and the solid residue is removed by filtration.

After evaporation of the solvent, 31 g of compound 1.3 are isolated, as a yellow solid (yield=62%) having the NMR characteristics hereafter:

$^1$H NMR (500 MHz, DMSO-d$^6$): 0.62 (m, 2H, C$\underline{H}_2$Si); 1.23 (t, 9H, $^3$J=6.0 Hz, OCH$_2$C$\underline{H}_3$); 1.59-1.68 (m, 4H, CH$_2$C$\underline{H}_2$CH$_2$); 1.96 (m, 2H, C$\underline{H}_2$CH$_2$Si); 2.64 (m, 16H, C$\underline{H}_2$N); 3.06 (m, 8H, C$\underline{H}_2$CO); 3.24 (m, 2H, CONHC$\underline{H}_2$); 3.82 (q, 6H, $^3$J=6.0 Hz, OC$\underline{H}_2$CH$_3$); 7.03 (m, 6H, CON$\underline{H}_2$).

$^{13}$C NMR (125 MHz, DMSO-d$^6$): 8.5 ($\underline{C}$H$_2$Si); 19.1 (OCH$_2$$\underline{C}$H$_3$); 24.8 (CH$_2$$\underline{C}$H$_2$CH$_2$); 25.9 (CH$_2$$\underline{C}$H$_2$CH$_2$); 55.4 ($\underline{C}$H$_2$N); 58.6 (O$\underline{C}$H$_2$CH$_3$); 171.5 ($\underline{C}$O); 175.8 (CO).

Mass spectroscopy (MALDI-TOF) m/z: 632.5 s [L]$^+$.

Grafting of the Precursor 1.3 on Silica Gel

Grafting is carried out by putting 27.7 g (i.e. 44 mmol) of precursor 1.3 in contact with 60 g of silica dehydrated by azeotropic distillation (Kieselgel 60 marketed by Merck; grain size fraction=0.25-0.40 mm; specific surface area=550 m$^2$ g$^{-1}$). The operation is performed under a nitrogen atmosphere, in 1.25 L of freshly distilled toluene and heated to 110° C., with mechanical stirring for 40 h.

The obtained modified gel is recovered at room temperature by filtration, washed with ethanol, with ether and then dried in vacuo and sieved. 64.4 g of modified silica gel Si2323TAM are thereby obtained having the characteristics hereafter:

RPE (copper-metal gel, T=100 K): g$_\perp$=2.10; g$_{//}$=2.23; a$_{//}$=147×10 cm$^{-1}$.

IR (diffuse reflection, KBr, cm$^{-1}$): 3305 ($\nu_{NH}$); 2946 ($\nu_{CH}$); 2820 ($\nu_{CH}$); 1673 ($\nu_{CO}$); 1092 ($\nu_{SiO}$); 795 ($\delta_{OSiO}$).

Elementary analysis of the nitrogen element: 0.32 mmol g$^{-1}$ (% N: 3.57%).

X fluorescence of copper: 0.24 mmol g$^{-1}$.

Specific surface area (BET): 338 m$^2$ g$^{-1}$.

Total volume total of adsorbed nitrogen: 0.46 cm$^3$ g$^{-1}$.

Average diameter of the pores (BJH): 40 Å (distribution 20-110 Å).

EXAMPLE 2

Preparation of the Material Si2223TAMMe$_2$ (Direct Condensation of a Macrocyclic Precursor Bearing a Silane Group on Silica Gel)

In this example, a material of formula Si2223TAMMe$_2$ as defined above in the present description was prepared, according to the reaction scheme hereafter:

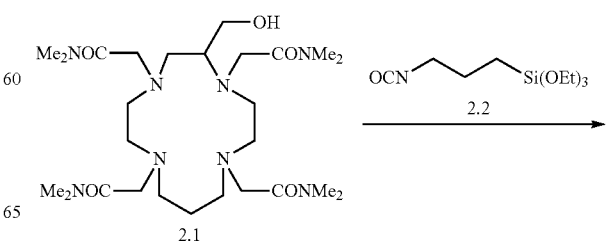

-continued

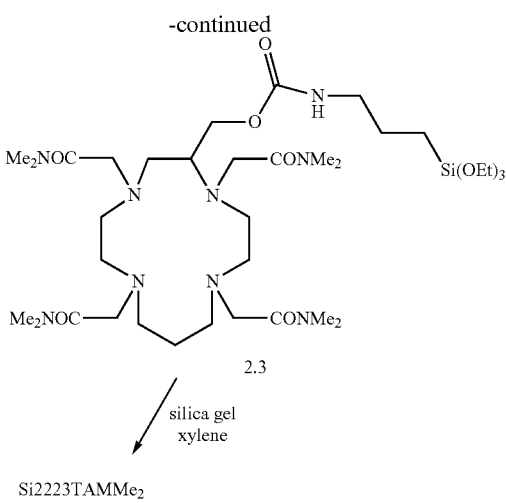

More specifically, the procedure hereafter was applied:

Preparation of Compound 2.1

The precursor 2.1 is obtained starting with tetraamine 1,4,7,10-tetraazacyclotridec-5-yl-methanol, the preparation of which was described in the international application WO 03/029228.

A solution containing 7.70 g (35.60 mmol) of tetraamine 1,4,7,10-tetraazacyclotridec-5-yl-methanol in 500 mL of acetonitrile and 39.36 g (284.80 mmol) of potassium carbonate is refluxed before adding in a single portion 21.66 g (176.20 mmol) of 2-chloro-N,N-dimethylacetamide. The mixture is then left under stirring and refluxed for 5 days.

After filtration on celite and evaporation of the solvent in vacuo, a residual red oil is obtained which is purified by chromatography on an alumina column (eluent: dichloromethane/methanol 98:2 v/v).

5.5 g of the compound 2.1 are then obtained, as a yellow oil (yield=28%) having the characteristics hereafter:

$^1$H NMR (500 MHz, CDCl$_3$): 1.56 (m, 2H); 2.39 (m, 1H); 2.45-3.10 (m, 14H); 2.85 (s, 3H); 2.87 (s, 9H); 2.93 (s, 3H); 2.97 (s, 3H); 3.01 (s, 3H); 3.02 (s, 3H); 3.15-3.6 (m, 11 H).

$^{13}$C NMR (125 MHz, CDCl$_3$): 24.2 (CH$_2$CH$_2$CH$_2$); 35.8 (3C, NCH$_3$); 36.1 (NCH$_3$); 36.8 (NCH$_3$); 37.1 (NCH$_3$); 37.4 (2C, NCH$_3$); 50.8 (2C, NCH$_2$); 50.9 (NCH$_2$); 51.5 (NCH$_2$); 52.1 (2C, NCH$_2$); 54.7 (NCH$_2$); 54.8 (NCH$_2$); 57.4 (2C, CH$_2$CO); 58.0 (CH$_2$CO); 60.2 (CH$_2$CO); 62.5 (CH$_2$OH); 170.9 (CO); 171.0 (CO); 171.1 (CO); 172.8 (CO).

Mass spectroscopy (MALDI-TOF) m/z: 557.7 [L]$^+$.

Preparation of Compound 2.3

To a solution of 7.40 g (13.29 mmol) of the compound 2.1 dissolved in 100 mL of dichloromethane in the presence of 3 mL of triethylamine, 3.90 g (i.e. 13.29 mmol) of the compound 2.2 (3-isocyanatopropyltriethoxysilane marketed by Aldrich—purity >95%) are added.

The mixture is stirred at room temperature for 12 h. Analysis by infrared spectroscopy gives the possibility of tracking the progression of the reaction and of noticing the disappearance of the characteristic band of the N=C=O function at 2272 cm$^{-1}$.

At the end of the reaction, the solvent is evaporated in vacuo thereby allowing isolation of the compound 2.3 as an orange oil, which is used without any further purification in the step below.

Grafting of the Precursor 2.3 on Silica Gel

Grafting is carried out by putting the whole of the compound 2.3 (orange oil) obtained in the previous step in contact with 31.00 g of silica, dehydrated by azeotropic distillation (Kieselgel 60—Merck; grain size fraction=0.25-0.40 mm; specific surface area=550 m$^2$ g$^{-1}$). The reaction is conducted in 250 mL of distilled xylene which are refluxed and mechanically stirred under an argon atmosphere for 72 h.

The modified gel is recovered at room temperature by filtration, washed with water, with ethanol and with chloroform, and then dried in vacuo and sieved.

34.90 g of modified silica gel Si2223CTAMMe$_2$ are thereby obtained, having the characteristics hereafter:

Elementary analysis of the nitrogen element: 0.22 mmol g$^{-1}$ (% N: 2.46%).

X fluorescence of copper: 0.15 mmol g$^{-1}$.

EXAMPLE 3

Preparation of the Material Si2323UENTAM (Direct Condensation of a Macrocyclic Precursor Bearing a Silane Group on Silica Gel)

In this example, a material of formula Si2323UENTAM as defined above in the present description was prepared according to the reaction scheme hereafter:

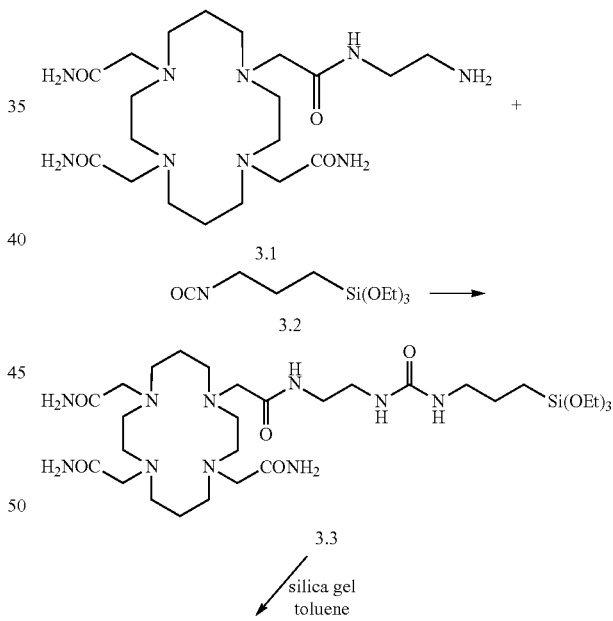

More specifically, the procedure below was applied:

Preparation of Compound 3.1

This compound is prepared according to the procedure described for the compound 4.2 of Example 4 hereafter.

Preparation of the Precursor 3.3

To a solution of 2.96 g (6.3 mmol) of compound 3.1 dissolved in 40 mL of freshly distilled absolute ethanol, 1.64 mL (6.3 mmol) of compound 3.2 (3-isocyanatopropyltriethoxysilane marketed by Aldrich, of purity >95%) are added. The mixture is heated and refluxed with ethanol for 24 h. Analysis by infrared spectroscopy gives the possibility of following the progression of the reaction and of noticing the disappearance of the characteristic band of the N=C=O function at 2272 cm$^{-1}$. The solvent is evaporated in vacuo and the compound 3.3 obtained is used as such in the following step.

Grafting of the Precursor 3.3 on Silica Gel

Grafting is carried out by putting 3.5 g (4.87 mmol) of precursor 3.3 in contact with 4.87 g of silica dehydrated by azeotropic distillation (Kieselgel 60—Merck; grain size fraction=0.25-0.40 mm; specific surface area=550 m$^2$ g$^{-1}$). The reaction is conducted in 50 mL of distilled toluene refluxed under mechanical stirring, under an argon atmosphere for 24 h.

The modified gel is recovered at room temperature by filtration, washed with toluene, with ethyl ether, and then dried in vacuo.

7.83 g of modified silica gel Si2323UENTAM are thereby obtained having the following characteristics:

Elementary analysis of the nitrogen element: 0.49 mmol g$^{-1}$ (% N: 6.86%).

EXAMPLE 4

Preparation of the Material Si2323ENTAM (Grafting Involving Nucleophilic Substitution)

In the present Example 4, as well as in both Examples 5 and 6 which follow, a material according to the invention is prepared by reacting an aminated precursor with silica gel grafted beforehand with compounds bearing —Cl functions (introduced by reaction of the silica with chloropropyltriethoxysilane compounds). This modified silica gel, so-called SiCl, which has the following structure:

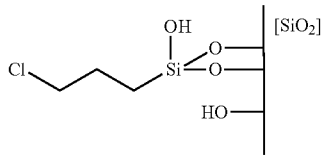

is prepared according to the procedure hereafter:

60 g of silica dehydrated by azeotropic distillation (Kieselgel 60—Merck; grain size fraction=0.25-0.40 mm; specific surface area=550 m$^2$ g$^{-1}$) and 6 g (25 mmol) of chloropropyltriethoxysilane are mixed in 100 mL of toluene under a nitrogen atmosphere. The obtained mixture is maintained refluxed with the solvent for 24 h. After filtration, washing with dichloromethane and drying, the material is sieved. The sought SiCl gel is thereby obtained which has the following properties:

IR (diffuse reflection, KBr, cm$^{-1}$): 3624 ($v_{OH}$); 2980 ($v_{CH}$); 2961 ($v_{CH}$); 2936 ($v_{CH}$); 2898 ($v_{CH}$); 1630 ($\delta_{OH}$); 1446 ($\delta_{CH2}$); 1395 ($\delta_{CH2}$); 1096 ($v_{SiO}$); 793 ($\delta_{OSiO}$).

Elementary analysis of the chlorine element: 0.3 mmol g$^{-1}$ (% Cl=1.02%).

Specific surface area (BET): 464 m$^2$ g$^{-1}$.

Total volume of adsorbed nitrogen: 0.61 cm$^3$ g$^{-1}$.

Average diameter of the pores (BJH): 55 Å (distribution 20-120 Å).

Specifically, in the present example 4, a material of formula Si2323ENTAM as defined above in the present description was prepared according to the reaction scheme hereafter:

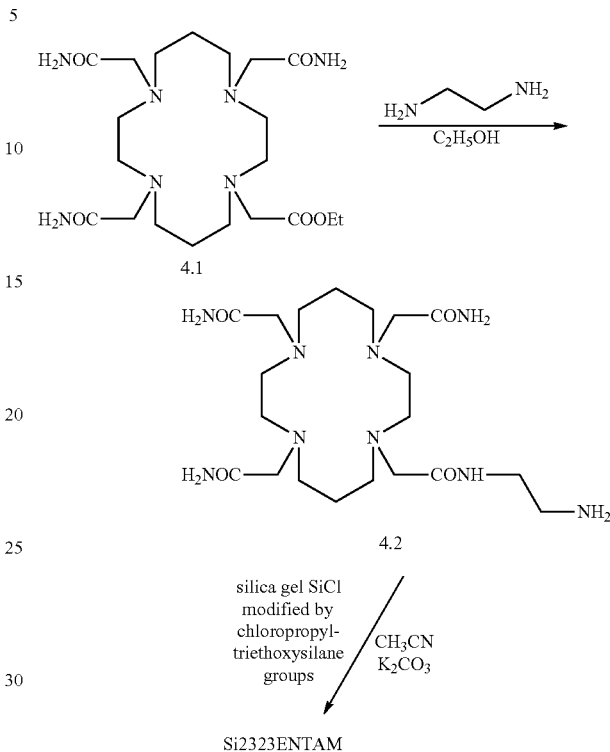

More specifically, the procedure hereafter was applied:

Preparation of Compound 4.1

The monoester 4.1 is prepared by maintaining for 48 h reflux of 1 L of acetonitrile containing 15 g (30 mmol) of triacetamide 1.1, 5 g (30 mmol) of ethyl bromoacetate and 10.5 g (75 mmol) of potassium carbonate.

After filtration and evaporation of the solvent, 13.5 g of the desired compound 4.1 are isolated as a white solid (yield=98%). The compound has the following characteristics:

$^1$H NMR (300 MHz, CDCl$_3$): 1.14 (t, 3H, $^3$J=6.0 Hz, OCH$_2$C$\underline{H}_3$); 1.55 (m, 4H, CH$_2$C$\underline{H}_2$CH$_2$); 2.50 (s, 16H, C$\underline{H}_2$N); 2.93 (s, 6H, C$\underline{H}_2$CONH$_2$); 3.14 (s, 2H, C$\underline{H}_2$COOEt); 4.02 (q, 2H, $^3$J=6.0 Hz, OC$\underline{H}_2$CH$_3$); 6.13 (s, 1H, CON$\underline{H}$); 6.68 (s, 2H, CON$\underline{H}$); 7.03 (s, 1H, CON$\underline{H}$); 7.22 (s, 1H, CON $\underline{H}$); 7.89 (s, 1H, CON$\underline{H}$).

$^{13}$C NMR (75 MHz, CDCl$_3$): 14.7 (OCH$_2$$\underline{C}$H$_3$); 26.0 (CH$_2$ $\underline{C}$H$_2$CH$_2$); 26.3 (CH$_2$$\underline{C}$H$_2$CH$_2$); 52.4-54.3 ($\underline{C}$H$_2$N); 56.1 ($\underline{C}$H$_2$N); 59.1 ($\underline{C}$H$_2$CONH$_2$); 59.4 ($\underline{C}$H$_2$COOEt); 61.4 (O$\underline{C}$H$_2$CH$_3$); 172.4 ($\underline{C}$OOEt); 176.3 ($\underline{C}$ONH$_2$); 176.5 ($\underline{C}$ONH$_2$); 176.95 ($\underline{C}$ONH$_2$).

Mass spectroscopy (MALDI-TOF) m/z: 458.3 [L+H]$^+$.

Preparation of the Precursor 4.2

Macrocyclic Precursor Bearing a Primary Amine

To 13 g (32.7 mmol) of the compound 4.1 dissolved in 700 mL of absolute ethanol, are added 200 equivalents of ethylenediamine (380 mL; 6.5 mol). The reaction mixture is maintained refluxed for 24 h under a nitrogen atmosphere. The solvent and the excess ethylenediamine are evaporated before drying the residue in vacuo (T=50° C., P=4 torrs).

The sought compound 4.2 is isolated as 13.7 g of a white powder (yield=89%), having the following characteristics:

$^1$H NMR (300 MHz, D$_2$O): 1.61 (m, 4H, CH$_2$C$\underline{H}_2$CH$_2$); 2.49-2.61 (m, 18H, C$\underline{H}_2$N); 3.03 (m, 8H, CH$_2$CO); 3.15 (t, 2H, $^3$J=6.4 Hz, CONHC$\underline{H}_2$).

$^{13}$C NMR (75 MHz, D$_2$O): 23.2 (CH$_2\underline{C}$H$_2$CH$_2$); 40.4-52.5 ($\underline{C}$H$_2$N); 57.8-58.7 ($\underline{C}$H$_2$CO); 174.7 ($\underline{C}$O); 177.0 ($\underline{C}$O); 177.7 ($\underline{C}$O).

Grafting of the Precursor 4.2 on SiCl Gel

Nucleophilic Substitution

Grafting is carried out by putting 15 g (32 mmol) of compound 4.2 in contact with 65 g of modified silica SiCl and 10 g (72 mmol) of potassium carbonate dissolved in 600 mL of acetonitrile. The medium is maintained refluxed under mechanical stirring for 48 h. After returning to room temperature, after filtration, drying and sieving, 70 g of a material Si2323ENTAM are obtained having the characteristics hereafter:

RPE (copper-metal gel, T=100 K): $g_\perp$=2.07; $g_{//}$=2.23; $a_{//}$=156×10$^4$ cm$^{-1}$.

IR (diffuse reflection, KBr, cm$^{-1}$): 3733 ($v_{OH}$); 3294 ($v_{OH}$); 2943 ($v_{CH}$); 2889 ($v_{CH}$); 1669 ($v_{CO}$); 1538 ($\delta_{CNH}$); 1456 ($v_{CN}$); 1087 ($v_{SiO}$); 797 ($\delta_{OSiO}$).

Elementary analysis of the nitrogen element: 0.18 mmol g$^{-1}$ (% N: 2.22%).

X fluorescence of copper: 0.18 mmol g$^{-1}$.

Specific surface area (BET): 368 m$^2$ g$^{-1}$.

Total volume of adsorbed nitrogen: 0.57 cm$^3$ g$^{-1}$.

Average diameter of the pores (BJH): 60 Å (distribution 20-120 Å).

EXAMPLE 5

Preparation of the Material Si2323ENTAMMe$_2$ (Grafting Involving Nucleophilic Substitution)

In this example, a material of formula Si2323ENTAMMe$_2$ as defined above in the present description was prepared according to the reaction scheme below:

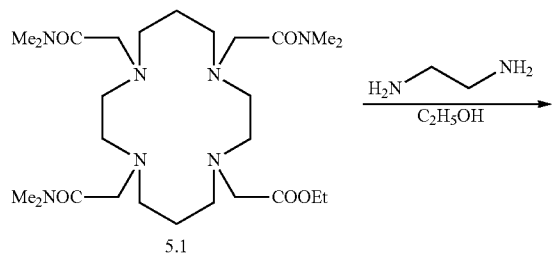

More specifically, the procedure hereafter was applied:

Preparation of Compound 5.1

The precursor 5.1 is prepared in two steps from cyclam.

In a first phase, ethyl (1,4,8,11-tetraazacyclotetradec-1-yl) ethanoate is obtained by slowly adding 6.68 g (40.0 mmol) of ethyl bromoacetate onto a solution of 40 g (200.0 mmol) of cyclam and 16 g (116 mmol) of potassium carbonate in 1 L of chloroform. The reaction mixture is maintained under stirring at room temperature for 48 h. After filtration on celite and evaporation of the solvent, the residue is taken up in petroleum ether. The excess cyclam is filtered off, the filtrate is concentrated and ethyl (1,4,8,11-tetraazacyclotetradec-1-yl) ethanoate (so-called compound 5.0) is thereby obtained, as 11.21 g of a slightly yellow oil (yield=98%) which is used without any purification.

The three secondary amines of the obtained monoester 5.0 are then functionalized with 2-chloro-N,N-dimethylacetamide (this chlorinated reagent is preferred to its brominated analog which leads to the formation of a significant amount of quaternized products). To do this, the 11.21 g (i.e. 39.2 mmol) of the compound 5.0 obtained previously are dissolved in 100 mL of acetonitrile and this solution is added dropwise into a solution of 14.28 g (117 mmol) of 2-chloro-N,N-dimethylacetamide and 35 g (252 mmol) of potassium carbonate in 900 mL of acetonitrile brought to 30° C. The reaction medium is maintained at 45° C. with stirring for 48 h.

After filtration on celite and evaporation of solvent, the compound 5.1 is obtained as 20.2 g of a slightly yellow solid (yield=95%), having the following characteristics:

$^1$H NMR (500 MHz, CDCl$_3$): 1.21 (t, 3H, OCH$_2$C$\underline{H}_3$); 1.57 (m, 4H, CH$_2$C$\underline{H}_2$CH$_2$); 2.50-2.63 (m, 16H, C$\underline{H}_2$N); 2.88 (s, 9H, NC$\underline{H}_3$); 3.04 (s, 3H, NC$\underline{H}_3$); 3.07 (s, 3H, NC$\underline{H}_3$); 3.10 (s, 3H, NC$\underline{H}_3$); 3.23-3.27 (m, 8H, C$\underline{H}_2$CONH$_2$ and C$\underline{H}_2$CO$_2$Et); 4.09 (q, 2H, OC$\underline{H}_2$CH$_3$).

$^{13}$C NMR (125 MHz, CDCl$_3$): 14.9 (OCH$_2\underline{C}$H$_3$); 25.2 (CH$_2\underline{C}$H$_2$CH$_2$); 25.4 (CH$_2\underline{C}$H$_2$CH$_2$); 36.1-38.1 (N$\underline{C}$H$_3$); 51.1-52.5 ($\underline{C}$H$_2$N); 56.0 ($\underline{C}$H$_2$CO$_2$Et); 57.8 ($\underline{C}$H$_2$CONH$_2$); 58.1 ($\underline{C}$H$_2$CONH$_2$); 58.4 ($\underline{C}$H$_2$CONH$_2$); 60.8 (O$\underline{C}$H$_2$CH$_3$); 171.3 ($\underline{C}$O$_2$Et); 171.5 ($\underline{C}$ONMe$_2$); 171.6 ($\underline{C}$ONMe$_2$); 172.0 ($\underline{C}$ONMe$_2$).

Mass spectroscopy (MALDI-TOF) m/z: 541.8 [L]$^+$.

Elementary analysis: C, 57.93; H, 9.70; N, 17.93. (As an indication, the data calculated for C$_{26}$H$_{51}$N$_7$O$_5$ (M=541.40) are the following: C, 57.65; H, 9.49; N, 18.10).

Preparation of the Precursor 5.2

Macrocyclic Precursor Bearing a Primary Amine

A solution of 12.09 g (22.33 mmol) of compound 5.1 and 240 mL (43 mol) of ethylenediamine in 900 mL of ethanol is refluxed with heating for 48 h.

After evaporation of the solvent and of the excess ethylenediamine, the compound 5.2 is obtained as 11.50 g of a slightly yellow solid (yield: 93%), having the following characteristics:

$^1$H NMR (500 MHz, CDCl$_3$): 1.39 (m, 4H, CH$_2$C$\underline{H}_2$CH$_2$); 2.27-2.52 (m, 20H, C$\underline{H}_2$N); 2.59 (s, 9H, NC$\underline{H}_3$); 2.71 (s, 3H, NC$\underline{H}_3$); 2.76 (s, 3H, NC$\underline{H}_3$); 2.82 (s, 3H, NC$\underline{H}_3$); 2.96-3.01 (m, 8H, CH$_2$CO); 7.66 (t, 1H, CON$\underline{H}$CH$_2$).

$^{13}$C NMR (125 MHz, CDCl$_3$): 24.5 (CH$_2$$\underline{C}$H$_2$CH$_2$); 25.0 ($\underline{C}$H$_2$$\underline{C}$H$_2$CH$_2$); 35.3-37.1 (N$\underline{C}$H$_3$); 41.7 ($\underline{C}$H$_2$N); 41.9 ( $\underline{C}$H$_2$N); 50.6-52.0 ($\underline{C}$H$_2$N); 56.0 ($\underline{C}$H$_2$CO); 56.7 ($\underline{C}$H$_2$CO); 57.4 ($\underline{C}$H$_2$CO); 58.4 ($\underline{C}$H$_2$CO); 170.1 ($\underline{C}$O); 170.4 ($\underline{C}$O); 170.6 ($\underline{C}$O); 172.2 ($\underline{C}$O).

Mass spectroscopy (MALDI-TOF) m/z: 556.2 [L+H]$^+$.

Grafting of the Precursor 5.2 on the SiCl Gel

Nucleophilic Substitution

Grafting is carried out by putting 10.27 g (18.5 mmol) of compound 5.2 in contact with 60 g of modified silica SiCl and 6.9 g (50 mmol) of potassium carbonate dissolved in 400 mL of acetonitrile. The medium is maintained under reflux with mechanical stirring for 48 h. After returning to room temperature, filtration, drying and sieving, 65 g of material Si2323ENTAMMe$_2$ are obtained having the characteristics hereafter:

RPE (copper-metal gel, T=100 K): g$_\perp$=2.07; g$_{//}$=2.23; a$_{//}$=156×10$^4$ cm$^{-1}$.

Elementary analysis of the nitrogen element: 0.18 mmol g$^{-1}$ (% N: 2.02%).

X fluorescence of copper: 0.10 mmol g$^{-1}$.

Specific surface area (BET): 356 m$^2$ g$^{-1}$.

Total volume of adsorbed nitrogen: 0.74 cm$^3$ g$^{-1}$.

Average diameter of the pores (BJH): 83 Å (distribution 30-160 Å).

EXAMPLE 6

Preparation of the Material Si2323CTAMMe$_2$ (Grafting Involving a Nucleophilic Substitution)

In this example, a material of formula Si2323CTAMMe$_2$ as defined earlier in the present description was prepared according to the reaction scheme hereafter:

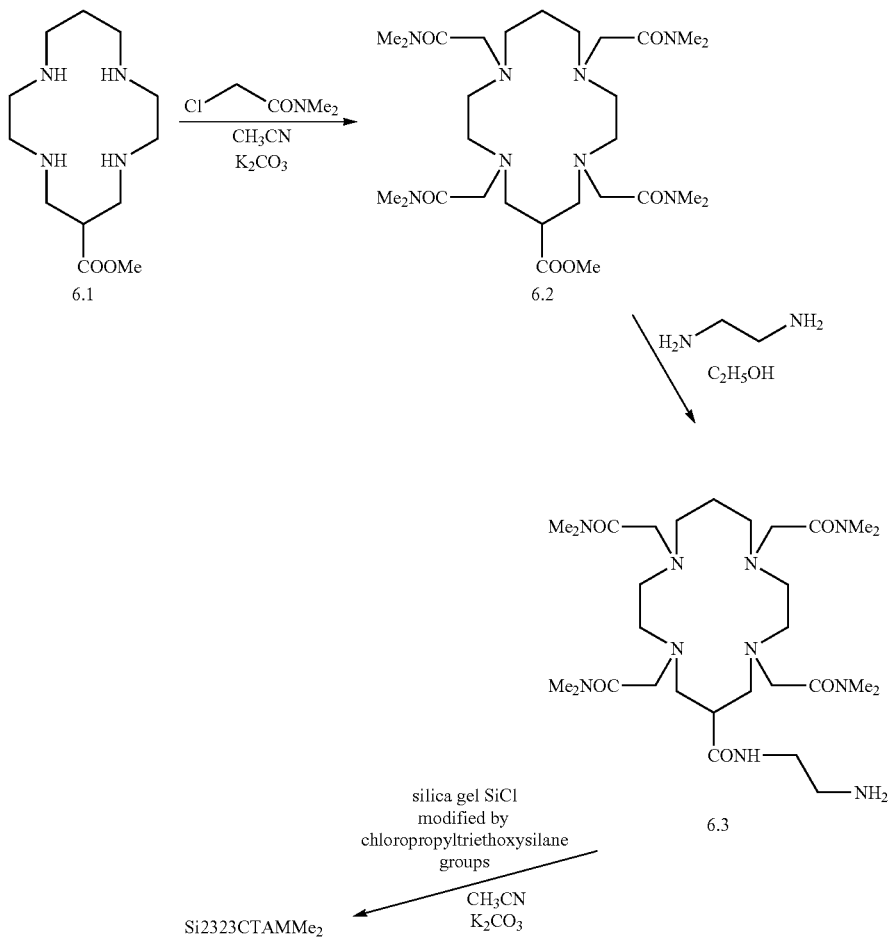

Preparation of Compound 6.2

The synthesis of the precursor 6.2 initially proceeds with the methyl ester 6.1 (methyl 1,4,8,11-tetraazacyclotetradecane-6-carboxylate), the synthesis of which was described in the application WO 03/029228. To 20.53 g (148.0 mmol) of potassium carbonate and 5.00 g (12.38 mmol) of the compound 6.1.4HCl dissolved in 500 mL of refluxed acetonitrile, are added in a single portion, 6.02 g (12.38 mmol) of 2-chloro-N,N-dimethylacetamide, and then the mixture is refluxed for 5 days with stirring. After filtration on celite and evaporation of the solvent, a yellow oil is obtained, which is purified by chromatography on an alumina column (eluent: dichloromethane and then dichloromethane/methanol 2:98 v/v). The head fraction corresponds to the compound 6.2 which is isolated as 3.70 g of a colorless oil after evaporating the solvent in vacuo (yield=62%), the obtained compound having the following characteristics:

$^1$H NMR (500 MHz, CDCl$_3$): 1.61 (m, 2H); 2.52-3.05 (m, 17H); 2.83 (s, 6H); 2.87 (s, 6H); 2.95 (s, 6H); 3.03 (s, 6H); 3.18 (d, 2H, $^3$J=14.0 Hz); 3.29 (d, 2H, $^3$J=14.0 Hz); 3.31 (s, 4H); 3.60 (s, 3H).

$^{13}$C NMR (125 MHz, CDCl$_3$): 25.2 (CH$_2$CH$_2$CH$_2$); 36.0 (NCH$_3$); 36.1 (NCH$_3$); 37.5 (NCH$_3$); 37.6 (NCH$_3$); 45.2 ( CHCO$_2$Me); 51.4 (CH$_2$N); 51.6 (CH$_2$N); 52.2 (CH$_2$N); 52.3 (CO$_2$CH$_3$); 55.9 (CH$_2$N); 58.3 (CH$_2$CO); 58.4 (CH$_2$CO); 171.1 (CONMe$_2$); 171.2 (CONMe$_2$); 176.0 (CO$_2$Me).

Mass spectroscopy (MALDITOF) m/z: 599.2 [M]$^+$.

Preparation of the Precursor 6.3

Macrocyclic Precursor Bearing a Primary Amine

A solution containing 28.0 g (46.76 mmol) of the monoester 6.2 prepared previously and 562.0 g (9.36 mol) of ethylenediamine dissolved in 1 L of ethanol is heated to 60° C. for 48 h. After evaporation of the solvent and of the excess ethylenediamine, the compound 6.3 is quantitatively isolated and is used without any subsequent purification in the next step.

Grafting of the Precursor 6.3 on SiCl Gel

Nucleophilic Substitution

A mixture consisting of 19.00 g (30.0 mmol) of the compound 6.3, 12.40 g (90.0 mmol) of potassium carbonate and 60.00 g of modified silica gel SiCl in 400 mL of acetonitrile are refluxed for 72 h with heating. After filtration and washing with water, ethanol and chloroform, and then drying, 64.1 g of a material Si2323CTAMMe$_2$ are obtained, having the following characteristics:

Elementary analysis of the nitrogen element: 0.10 mmol g$^{-1}$ (% N: 1.12%).

X fluorescence of copper: 0.11 mmol g$^{-1}$.

EXAMPLE 7

Preparation of the Material Si2323TAM (Grafting Involving Catalytic Hydrosilylation)

In this Example 7 and in Examples 8 and 9 which follow, a material according to the invention was prepared by reacting a precursor bearing a vinyl end group with silica gel treated with triethoxysilane. This silica gel which will be designated hereafter by "SiH", was prepared by following the procedure described by Chu et al. in *Anal. Chem.*, Vol. 65, pp. 808-816 (1993). More specifically, 5 g of silica dehydrated by azeotropic distillation (Kieselgel 60-Merck; grain size fraction=0.25-0.40 mm; specific surface area=550 m$^2$ g$^{-1}$) are suspended in 100 mL of dioxane also containing 1.6 mL of a 35% hydrochloric acid solution. The mixture is mechanically stirred and heated to 75° C. before introducing over a period of 15 min, 3.7 g (22.5 mmol) of triethoxysilane diluted in 45 mL of dioxane. Heating is maintained for 1 h before filtering the mixture and drying the gel. The modified gel SiH obtained has the following characteristics:

IR (diffuse reflection, KBr, cm$^{-1}$): 2250 ($v_{SiH}$).

In the present Example 7, a precursor 7.2 of the following formula was grafted:

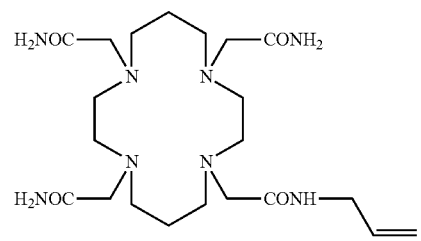

7.2 on the SiH gel.

This compound 7.2 was obtained starting with a precursor 7.1 according to the following procedure:

Preparation of the Precursor 7.1

Under a nitrogen atmosphere, 10.6 mL (133 mmol) of chloroacetyl chloride and 30 g (266 mmol) of potassium carbonate are mixed in 500 mL of dichloromethane. The mixture is cooled to 0° C.

20 mL (133 mmol) of allylamine dissolved in 50 mL of dichloromethane are then added. The addition is carried out over a period of 15 minutes by means of an isobaric dropping funnel. Stirring is maintained at room temperature for 18 h and the mixture is then filtered on celite. By evaporating the solvent, the compound 7.1 is obtained as 16.3 g of a pale yellow oil (yield=92%), having the following characteristics:

$^1$H NMR (200 MHz, CDCl$_3$): 3.87 (t, 2H, $^3$J=5.7 Hz, CONHCH$_2$); 4.03 (s, 2H, CH$_2$Cl); 5.09 (d, 1H, $^3$J$_{cis}$=12 Hz, CH=CH$_2$); 5.13 (d, 1H, $^3$J$_{trans}$=17 Hz, CH=CH$_2$); 5.80 (ddt, 1H, $^3$J=5.7 Hz, $^3$J$_{cis}$=12 Hz, $^3$J$_{trans}$=17 Hz, CH=CH$_2$); 6.87 (broad s, 1H, CONH).

$^{13}$C NMR (50 MHz, CDCl$_3$): 42.4 (NHCH$_2$); 42.8 (Cl CH$_2$); 117.2 (CH=CH$_2$); 133.3 (CH=CH$_2$); 166.6 (CO).

Preparation of Compound 7.2

The vinyl precursor 7.2 is synthesized from the compound 1.1 prepared in Example 1 (i.e. the trisubstituted compound TE3AM.HI). More specifically, 10 g (20 mmol) of the compound 1.1 are dissolved in 100 mL of water and the solution is set to boil. 2.67 g (20 mmol) of the compound 7.1 are then added in a single portion, to the boiling medium, while maintaining the pH of the medium above 12 by adding benzyltrimethylammonium hydroxide (in a 40% (by mass) aqueous solution). Heating is maintained for 2 h under these conditions, and then the solvent is removed by evaporation in vacuo, whereby an oily yellow residue is obtained. Addition of 100 mL of acetone and 20 mL of ethanol to this residue leads to precipitation of a while solid which is isolated, washed with 100 mL of acetone and 100 mL of ether and then dried in vacuo, whereby 5.5 g of the sought compound 7.2 are obtained (yield=59%), having the characteristics hereafter:

$^1$H NMR (200 MHz, D$_2$O+DCl, pD<1): 2.10 (m, 4H, CH$_2$CH$_2$CH$_2$); 3.38 (m, 8H, CH$_2$N); 3.64-3.71 (m, 10H, CH$_2$N+CONHCH$_2$); 4.02 (broad s, 8H, CH$_2$CO); 5.00 (m, 1H, CH=CH$_2$); 5.03 (m, 1H, CH=CH$_2$); 5.64 (m, 1 H, CH=CH$_2$).

$^{13}$C NMR (50 MHz, D$_2$O+DCl, pD<1): 18.58 (CH$_2$CH$_2$CH$_2$); 42.34 (CONHCH$_2$); 46.38 (CH$_2$N); 50.17 (CH$_2$N); 56.80 (CH$_2$CONH$_2$); 57.08 (CH$_2$CONH); 116.75 (CH=CH$_2$); 133.38 (CH=CH$_2$); 164.92 (CONH); 167.35 (CONH$_2$).

IR (KBr, cm$^{-1}$): 3392 ($v_{NH}$); 2925 ($v_{CH}$); 2879 ($v_{CH}$); 2827 ($v_{CH}$); 1679 ($v_{CO}$); 1597 ($v_{C=C}$); 1384 ($v_{CN}$); 1159 ($v_{CN}$); 1060 ($\delta_{CH\,allyl}$); 623 ($\omega_{NH}$).

Mass spectroscopy (MALDI-TOF) m/z: 468.9 [L+H]$^+$; 490.7 [L+Na]$^+$; 506.2 [L+K]$^+$.

Grafting of the Precursor 7.2 on SiH Silica Gel 1 g of SiH gel and 1 mmol of compound 7.2 are mixed with mechanical stirring in 50 mL of ethanol containing 2% molar of hydrosilylation catalyst (40% Pt hexachloroplatinic acid hydrate). The reaction medium is brought to 80° C. for 48 h. The material is then recovered by filtration, washed with ethanol, with water and then with acetone, before being dried in vacuo. It has the following characteristics:

IR (diffuse reflection, KBr, cm$^{-1}$): 3300 ($v_{NH}$); 2977 ($v_{CH}$); 2820 ($v_{CH}$); 1665 ($v_{CO}$); 1092 ($v_{SiO}$); 792 ($\delta_{OSiO}$).

Elementary analysis of the nitrogen element: 0.11 mmol g$^{-1}$ (% N: 1.28%).

Comments:

The grafting mode described here is purely an indication and may be modified to quite an extent. For example a solvent other than ethanol (2-propanol or acetonitrile notably) may be used and/or another hydrosilylation catalyst such as for example a Wilkinson catalyst may be used.

Moreover, in situ grafting of the precursors on a non-modified silica gel may alternatively be used, by reversing the addition order of the triethoxysilane. In this case, the vinyl or styrene precursor is first silylated via a catalytic route with an agent such as (40% Pt) hexachloroplatinic acid hydrate or the Wilkinson reagent, and then the obtained reagent is condensed in situ on the silanol functions of a non-modified dehydrated silica gel.

These comments are valid for the graftings described in Examples 8 and 9 which follow.

EXAMPLE 8

Preparation of the Material Si2323TAMMe$_2$ (Grafting Involving Catalytic Hydrosilylation)

In this example, a precursor 8.2 of the following formula was grafted:

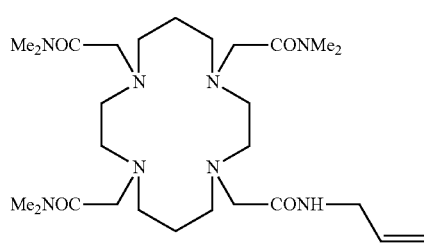

8.2 on the aforementioned SiH gel.

This compound 8.2 was obtained starting with a precursor 8.1, itself obtained from the precursor 7.1 of the previous Example 7, according to the procedure detailed hereafter:

Preparation of the Precursor 8.1 from the Precursor 7.1

5 g (25 mmol) of cyclam (1,4,8,11-tetraazacyclotetradecane), 830 mg (6.25 mmol) of the compound 7.1 prepared in Example 7, and 2.6 g (18.75 mmol) of potassium carbonate are mixed in 100 mL of tetrahydrofurane, and then the mixture is refluxed for 16 h. After evaporation of the solvent in in vacuo, a residue is obtained which is extracted with 3×100 mL of pentane. The obtained organic phase is filtered and the solvent is evaporated, whereby the product 8.1 is obtained as 1.65 g of a white oil (yield=88%), having the characteristics hereafter:

$^1$H NMR (300 MHz, CDCl$_3$): 1.65 (m, 4H, CH$_2$CH$_2$CH$_2$); 2.50-2.70 (m, 16 H, CH$_2$N); 3.02 (s, 2H, CH$_2$CO); 3.84 (m, 2H, CONHCH$_2$); 5.04 (d, 1H, $^3$J$_{cis}$=10.0 Hz, CH=CH$_2$); 5.13 (d, 1H, $^3$J$_{trans}$=17.0 Hz, CH=CH$_2$); 5.80 (ddt, 1H, $^3$J=5.5 Hz, $^3$J$_{cis}$=10.0 Hz, $^3$J$_{trans}$=17.0 Hz; CH=CH$_2$); 8.63 (broad s, 1H, CONH).

$^{13}$C NMR (75 MHz, CDCl$_3$): 26.88 (CH$_2$CH$_2$CH$_2$); 29.08 (CH$_2$CH$_2$CH$_2$); 41.93 (CONHCH$_2$); 47.66 (CH$_2$N); 48.19 (CH$_2$N); 48.57 (CH$_2$N); 49.11 (CH$_2$N); 49.32 (CH$_2$N); 50.87 (CH$_2$N); 54.13 (CH$_2$N); 56.72 (CH$_2$N); 58.53 (CH$_2$N); 116.13 (CH=CH$_2$); 135.56 (CH=CH$_2$); 171.98 (CO).

Mass spectroscopy (MALDI-TOF) m/z: 298.1 [L+H]$^+$.

Preparation of Compound 8.2

The compound 8.2 was obtained by trifunctionalization of the macrocyclic precursor 8.1. To do this, 2.7 g (9.09 mmol) of compound 8.1 was reacted with 3.3 g (27.3 mmol) of 2-chloro-N,N-dimethylacetamide, in the presence of 9 g (75 mmol) of potassium carbonate, in 350 mL of refluxed acetonitrile. After 48 h of reaction, the solvent is evaporated in vacuo and the residue is extracted with 200 mL of chloroform. After removing the solvent, an oil is obtained which is diluted in 200 mL of acetone. By evaporating the solvent, 3.0 g of the sought compound 8.2 (yield=60%) are obtained, having the characteristics hereafter:

$^1$H NMR (500 MHz, CDCl$_3$): 1.79 (m, 4H, CH$_2$CH$_2$CH$_2$); 2.74-2.82 (m, 16H, CH$_2$N); 3.07-3.32 (m, 18H, NCH$_3$); 3.45 (m, 8H, CH$_2$CO); 4.04 (m, 2H, CONHCH$_2$); 5.27 (d, 1H, $^3$J$_{cis}$=10.0 Hz, CH=CH$_2$); 5.33 (d, 1H, $^3$J$_{trans}$=16.2 Hz, CH=CH$_2$); 6.00 (m, 1H, CH=CH$_2$); 8.19 (s, 1H, CONH).

$^{13}$C NMR (125 MHz, CDCl$_3$): 25.34 (CH$_2$CH$_2$CH$_2$); 25.91 (CH$_2$CH$_2$CH$_2$); 35.67 (CONMe); 35.82 (CONMe); 36.03 (CONMe); 37.02 (CONMe); 37.32 (CONMe); 37.50 (CONMe); 42.03 (CONHCH$_2$); 50.91 (CH$_2$N); 51.37 (CH$_2$N); 51.87 (CH$_2$N); 52.08 (CH$_2$N); 52.50 (CH$_2$N); 52.63 (CH$_2$N); 53.10 (CH$_2$N); 53.40 (CH$_2$N); 55.80 (CH$_2$N); 57.19 (CH$_2$N); 57.90 (CH$_2$N); 116.60 (CH=CH$_2$); 135.08 (CH=CH$_2$); 170.52 (CONMe$_2$); 170.85 (CONMe$_2$); 171.10 (CONMe$_2$); 172.27 (CONH).

IR (KBr, cm$^{-1}$): 3434 ($v_{NH}$); 2941 ($v_{CH}$); 2797 ($v_{CH}$); 1643 ($v_{CO}$); 1412 ($v_{CN}$); 1119 ($v_{CN}$).

Mass spectroscopy (MALDI-TOF) m/z: 553.3 [L+H]$^+$; 575.0 [L+Na]$^+$.

Elementary analysis: C, 57.93; H, 9.62; N, 19.67. (for information, the values calculated for C$_{27}$H$_{52}$N$_8$O$_4$ (M=552.75) are C, 58.67; H, 9.48; N, 20.27).

Grafting of the Precursor 8.2 on Silica Gel SiH 1 g of SiH gel and 1 mmol of compound 8.2 are mixed with mechanical stirring in 50 mL of ethanol containing 2% molar of a hydrosilylation catalyst (40% Pt hexachloroplatinic acid hydrate). The reaction medium is brought to 80° C. for 48 h. The material is then recovered by filtration, washed with ethanol, with water and then with acetone, before being dried in vacuo. The obtained material Si2323TAMMe$_2$ has the following characteristics:

Elementary analysis of the nitrogen element: 0.08 mmol g$^{-1}$ (% N: 0.89%).

EXAMPLE 9

Preparation of the Material Si2323TAMvinyl (Grafting Involving Catalytic Hydrosilylation)

In this example, a precursor 9.2 of the formula was grafted:

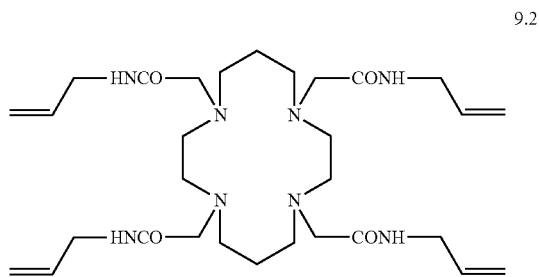

9.2 on the aforementioned SiH gel.

The compound 9.2 was obtained starting with the precursor 7.1 of the previous Example 7, according to the procedure hereafter:

Preparation of the Precursor 9.2 from the Precursor 7.1

To a solution of 5 g (25 mmol) of cyclam (1,4,8,11-tetraazacyclotetradecane) dissolved in 50 mL of water heated to 80° C. and kept under stirring, 16.6 g (125 mmol) of the compound 7.1 of Example 7 are added all at a time. The reaction medium is left at 80° C. for 15 minutes while maintaining the pH of the medium at a value above 12 by adding KOH tablets. The medium is then left under stirring without heating for 30 minutes more. The formed compound 9.2 is extracted from the reaction medium by extraction with 3×50 mL of chloroform. The fractions are collected, the organic phase is dried, the solvent is evaporated in vacuo, and then the obtained yellow residue is recrystallized from acetone, whereby the compound 9.2 is obtained as 4.07 g of fine transparent needles (yield=28%), having the characteristics hereafter:

$^1$H NMR (500 MHz, CDCl$_3$): 1.64 (p, 4H, $^3$J=6.7 Hz, CH$_2$C$\underline{H}_2$CH$_2$); 2.52 (t, 8H, $^3$J=6.7 Hz, CH$_2$CH$_2$C$\underline{H}_2$N); 2.58 (s, 8H, CH$_2$C$\underline{H}_2$N); 3.01 (s, 8H, C$\underline{H}_2$CO); 3.83 (t, 8H, $^3$J=6.0 Hz, CONHC$\underline{H}_2$); 5.11 (d, 4H, $^3$J$_{cis}$=10.0 Hz, C$\underline{H}$=CH$_2$); 5.17 (d, 4H, $^3$J$_{trans}$=17.0 Hz, C$\underline{H}$=CH$_2$); 5.80 (ddt, 4H, $^3$J=6.0 Hz, $^3$J$_{cis}$=10.0 Hz, $^3$J$_{trans}$=17.0 Hz, C$\underline{H}$=CH$_2$); 7.10 (t, 4H, $^3$J=6.0 Hz, CON$\underline{H}$).

$^{13}$C NMR (125 MHz, CDCl$_3$): 25.46 (CH$_2$$\underline{C}$H$_2$CH$_2$); 42.05 (CONH$\underline{C}$H$_2$); 51.21 ($\underline{C}$H$_2$N); 52.63 ($\underline{C}$H$_2$N); 58.61 ($\underline{C}$H$_2$CO); 117.59 (CH=$\underline{C}$H$_2$); 134.48 ($\underline{C}$H=CH$_2$); 170.87 ($\underline{C}$ONH).

IR (KBr, cm$^{-1}$): 3283 ($v_{NH}$); 3062 ($v_{CH\ allyl}$); 2980 ($v_{CH}$); 2951 ($v_{CH}$); 2925 ($v_{CH}$); 2830 ($v_{CH}$); 1649 ($v_{CO}$); 1551 ($v_{C=C}$); 1260 ($v_{CN}$); 996 ($\delta_{CH\ allyl}$); 929 ($\delta_{CH\ allyl}$); 709 ($\omega_{NH}$).

Mass spectroscopy (MALDI-TOF) m/z: 589.3 [L+H]$^+$; 610.8 [L+Na]$^+$; 626.7 [L+K]$^+$.

Grafting of the Precursor 9.2 on Silica Gel SiH 1 g of SiH gel and 1 mmol of compound 9.2 are mixed with mechanical stirring in 50 mL of ethanol containing 2% molar of a hydrosilylation catalyst (40%-Pt hexachloroplatinic acid hydrate). The reaction medium is brought to 80° C. for 48 h. The material is then recovered by filtration, washed with ethanol, with water and then with acetone before being dried in vacuo. The obtained material Si2323TAMvinyl has the following characteristics:

IR (diffuse reflection, KBr, cm$^{-1}$): 3733 ($v_{SiOH}$); 3700-3200 ($v_{OH}$+$v_{NH}$); 3080 ($v_{CH\ allyl}$); 2982 ($v_{CH}$); 2938 ($v_{CH}$); 2891 ($v_{CH}$); 1656 ($v_{CO}$); 1534 ($\delta_{CNH}$); 1090 ($v_{SiO}$); 803 ($\delta_{OSiO}$).

Elementary analysis of the nitrogen element: 0.21 mmol g$^{-1}$ (% N: 2.31%).

EXAMPLE 10

Example of Application of the Material Si2323TAM

Purification of Water of the Type Lead-Contaminated Drinking Water (Chromatography Column)

In this example, the extracting properties of the material Si2323TAM as prepared in Example 1 are demonstrated, towards different cations present in drinking water artificially contaminated with Pb$^{2+}$ cations.

The contaminated water used for the test is drinking water having the following physico-chemical characteristics:

| | |
|---|---|
| Temperature: | 17.6° C. |
| pH at 25° C.: | 7.7 |
| Alkalimetric titer: | 0° F. |
| Complete alkalimetric titer: | 23° F. (i.e. 4.6 meq/L) |
| Hydrometric titer: | 28.0° F. (i.e. 134 meq/L) |
| Lead concentration | 710 micrograms per liter. |
| Copper concentration | 160 micrograms per liter. |
| Zinc concentration | 550 micrograms per liter. |
| Magnesium concentration | 3.9 milligrams per liter. |
| Calcium concentration | 95.0 milligrams per liter. |
| Strontium concentration | 136 micrograms per liter. |
| Barium concentration | 17 micrograms per liter. |

The water was contaminated by dissolving lead nitride to saturation and then filtered, whereby an initial Pb$^{2+}$ cation content of 710 micrograms per liter was obtained.

The thereby contaminated water was percolated in a bed containing 50 g of the extracting material Si2323TAM contained in a chromatography column with a diameter equal to 2.5 cm, by means of a peristaltic pump having a flow rate of 1 L/h.

10 mL samples were regularly taken at the column outlet. Each sample was acidified to 2% with ultra pure nitric acid, and then analyzed by atomic emission spectrometry with inductively coupled plasma (ICP-AES).

The change in the concentration of the different elements Pb, Cu, Zn, Mg, Ca, Sr, Ba is copied out in Table 1 below, wherein:

V designates the accumulated volume of taken samples (in liters);

[Pb], [Cu], [Zn], [Mg], [Ca], [Sr], and [Ba] designate the concentrations of the respective elements (in micrograms per liter except for Mg and Ca where they are expressed in milligrams per liter).

TABLE 1

Cation concentration at the outlet of the column

| V (L) | [Pb] (µg L$^{-1}$) | [Cu] (µg L$^{-1}$) | [Zn] (µg L$^{-1}$) | [Mg] (mg L$^{-1}$) | [Ca] (mg L$^{-1}$) | [Sr] (µg L$^{-1}$) | [Ba] (µg L$^{-1}$) |
|---|---|---|---|---|---|---|---|
| 0.1 | 1.9 | 0.9 | 0.3 | 3.7 | 88.0 | 142.4 | 24.1 |
| 0.2 | 1.2 | 0.8 | 0.2 | 3.9 | 94.0 | 138.0 | 17.8 |
| 0.3 | 0.6 | 0.9 | 0.1 | 3.9 | 95.0 | 138.5 | 17.4 |
| 0.4 | 1.3 | 1.1 | 0.3 | 3.9 | 95.0 | 136.8 | 17.2 |
| 0.5 | 1.2 | 0.9 | 0.1 | 3.9 | 96.0 | 138.4 | 17.3 |
| 0.6 | 0.6 | 1.0 | 0.3 | 3.9 | 97.0 | 138.6 | 17.3 |
| 0.7 | 1.9 | 1.1 | 0.2 | 3.9 | 97.0 | 138.5 | 17.3 |
| 0.8 | 0.8 | 1.1 | 0.6 | 3.9 | 97.0 | 138.7 | 17.4 |
| 0.9 | 1.6 | 1.0 | 0.4 | 3.9 | 97.0 | 138.4 | 17.3 |
| 1.0 | 0.6 | 1.1 | 0.5 | 3.9 | 98.0 | 139.5 | 17.4 |
| 1.1 | 2.2 | 1.1 | 0.7 | 3.9 | 98.0 | 140.4 | 17.5 |
| 1.2 | 0.5 | 1.1 | 0.5 | 3.9 | 98.0 | 139.2 | 17.3 |
| 1.3 | 1.8 | 1.1 | 0.4 | 3.9 | 97.0 | 137.6 | 17.1 |
| 1.4 | 0.2 | 1.2 | 0.2 | 3.9 | 97.0 | 137.6 | 17.1 |
| 1.5 | 1.3 | 1.1 | 0.6 | 3.9 | 97.0 | 137.3 | 17.0 |
| 1.6 | 1.3 | 1.2 | 0.6 | 3.9 | 97.0 | 137.5 | 17.1 |
| 1.7 | 2.4 | 1.3 | 0.5 | 3.9 | 97.0 | 136.9 | 17.0 |
| 1.8 | 0.9 | 1.3 | 0.6 | 3.9 | 97.0 | 137.0 | 17.0 |
| 1.9 | 1.0 | 1.3 | 0.5 | 3.9 | 97.0 | 137.3 | 17.1 |
| 2.0 | 1.8 | 1.3 | 0.6 | 3.9 | 97.0 | 138.0 | 17.1 |
| 2.1 | 0.3 | 1.5 | 0.6 | 3.9 | 97.0 | 137.0 | 17.0 |
| 2.2 | 1.4 | 1.4 | 0.5 | 3.9 | 98.0 | 137.9 | 17.1 |
| 2.3 | 0.3 | 1.4 | 0.7 | 3.9 | 98.0 | 137.2 | 17.1 |
| 2.4 | 1.8 | 1.3 | 0.7 | 3.9 | 98.0 | 138.5 | 17.1 |
| 2.5 | 0.4 | 1.4 | 0.9 | 3.9 | 97.0 | 136.0 | 17.0 |
| 2.6 | 2.3 | 1.6 | 0.7 | 3.9 | 98.0 | 137.0 | 17.0 |
| 2.7 | 1.1 | 1.7 | 0.9 | 3.9 | 97.0 | 136.3 | 17.0 |
| 2.8 | 1.5 | 1.4 | 0.8 | 3.9 | 98.0 | 137.6 | 17.1 |
| 2.9 | 0.3 | 1.6 | 0.9 | 3.9 | 97.0 | 137.2 | 17.1 |
| 3.0 | 2.2 | 1.6 | 0.9 | 3.9 | 98.0 | 137.6 | 17.2 |
| 3.1 | 0.4 | 1.6 | 0.9 | 3.9 | 98.0 | 137.4 | 17.0 |
| 3.2 | 3.1 | 1.8 | 0.8 | 3.9 | 98.0 | 137.4 | 17.1 |
| 3.3 | 2.0 | 1.8 | 0.9 | 3.9 | 97.0 | 136.1 | 17.0 |
| 3.4 | 2.0 | 1.6 | 1.0 | 3.9 | 98.0 | 136.4 | 17.1 |
| 3.5 | 0.5 | 1.7 | 0.8 | 3.9 | 98.0 | 137.4 | 17.1 |
| 3.6 | 2.1 | 1.8 | 1.0 | 3.9 | 98.0 | 136.9 | 17.1 |
| 3.7 | 1.9 | 1.7 | 1.2 | 3.9 | 98.0 | 137.2 | 17.0 |
| 3.8 | 1.0 | 2.1 | 1.5 | 3.9 | 97.0 | 136.3 | 17.1 |
| 3.9 | 1.0 | 1.9 | 1.0 | 3.9 | 98.0 | 137.7 | 17.3 |
| 4.0 | 1.9 | 1.9 | 1.0 | 3.7 | 94.0 | 131.4 | 16.5 |
| 4.1 | 1.4 | 1.5 | 0.7 | 3.7 | 94.0 | 132.1 | 16.6 |
| 4.2 | 1.6 | 6.8 | 3.8 | 3.7 | 93.0 | 131.2 | 16.4 |
| 4.3 | 1.3 | 1.9 | 1.3 | 3.7 | 94.0 | 132.5 | 16.5 |
| 4.4 | 1.6 | 2.1 | 1.0 | 3.7 | 93.0 | 132.2 | 16.4 |

The observed results demonstrate excellent selectivity of the material which does bind earth alkaline metals but efficiently retains lead, copper and zinc.

EXAMPLE 11

Example of Application of the Material Si2323ENTAM

Purification of Water of the Lead-Contaminated Drinking Water Type (Filtering Cartridge)

In this example, the material Si2323ENTAM as prepared in Example 4 was used in a filtering cartridge of the type described for example in patent JP 02 301469, which is attached to the outlet tap of a sink.

More specifically, the cartridge of cylindrical shape (outer diameter: 6 cm; inner diameter: 5.5 cm, length: 9 cm) comprises:
- a central portion (diameter: 2.5 cm) consisting of a bundle of hollow fibers developing a surface area of about 0.1 m$^2$; and
- a hollow annular portion around this central portion, with a volume of 110 mL. This annular portion is intended to receive an extracting material, and in the present example it is filled with the material Si2323ENTAM.

The cartridge is provided with a side inlet for the water to be treated at the base of the annular portion and with an outlet for the treated water at the base of the bundle of hollow fibers of the central portion. Moreover, the high portion of the annular portion and the high portion of the central portion are in fluidic connection. Thus, the water which penetrates into the cartridge when the tap is opened, fills the annular portion (inflow of the water through the base improves the distribution of the fluid in the annular portion and reduces the probability of flow through preferential paths dug in the bed of the material), and then, having arrived in the high portion of the annular portion, the water passes into the central portion and flows through the bundle of hollow fibers in order to reach the outlet of the cartridge.

In the present example, several tests were carried out in which lead-contaminated water obtained by letting drinking water stagnate for 30 minutes in a lead pipe with a volume of 4.4 L connected on one side to the drinking water supply network and on the other side to a tap provided with the cartridge described earlier.

In each of the conducted tests, a complete purge of the pipe was first carried out by letting 30 L of water flow through it. The water was then left to stagnate in the pipe, by closing the tap for 30 minutes. After having carried out a 250 mL purge upstream and downstream from the cartridge, 2 L of water from the pipe were sampled. The flow rate of the water exiting the cartridge in the conducted tests is 110 liters per hour.

For each of the tests, the taken 2 L sample was homogenized by stirring, and then a 10 mL sample was taken which was acidified to 2% by ultra pure nitric acid, and then analyzed by inductively coupling plasma atomic emission spectrometry (ICP-AES).

In each case, the lead content measured in the water stemming from the treatment with the filtering cartridge was compared with that of the water of the first collected jet upstream from the cartridge during the initial purge.

The results are copied out in Table 2 hereafter, wherein [Pb]$_i$ designates the initial lead concentration, i.e. measured in the water of the first jet, and [Pb]$_f$ designates the final lead concentration, i.e. measured at the outlet of the cartridge. The values of these concentrations are given in micrograms per liter.

TABLE 2

Reduction in the Pb concentration by passing into the filtering cartridge

| | test | | | | | | | | | | |
|---|---|---|---|---|---|---|---|---|---|---|---|
| | 1 | 2 | 3 | 4 | 5 | 6 | 7 | 8 | 9 | 10 | 11 |
| [Pb]$_i$ | 53 | 78 | 73 | 65 | 77 | 647 | 61 | 511 | 541 | 518 | 53 |
| [Pb]$_f$ | 9 | 7 | 5 | 6 | 6 | 6 | 7 | 3 | 4 | 4 | 5 |

The results above conspicuously bring out the efficiency of the material Si2323ENTAM for retaining Pb$^{2+}$ cations, with a very low lead content at the output, systematically less than 10 micrograms per liter.

The invention claimed is:

1. A material adapted for extracting metal cations in an aqueous medium, comprising polyazacycloalkane compounds (PACs) immobilized on a solid support (S), the material fitting the following formula (Ia):

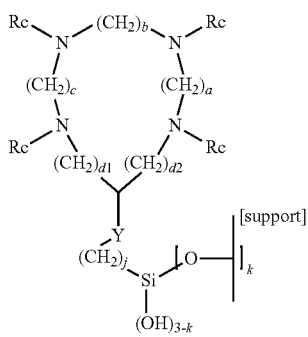

wherein:
- a, b and c are three integers, either identical or different, each of a, b and c being equal to 2 or 3;
- d1 and d2 are two integers, either identical or different, equal to 0, 1 or 2, it being understood that the sum (d1+d2) has the value 1 or 2;
- —Y— is a saturated or unsaturated, linear or branched divalent hydrocarbon group;
- j is an integer equal to 0, 1, 2 or 3; and
- k, which represents the number of bonds between the cyclic species and the solid support (S), is an integer equal to 1, 2 or 3; and
- each of the 4 Rc groups, either identical or different, represents a group fitting the general formula:

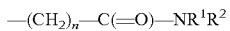

wherein n=1, 2 or 3; and
$R^1$ and $R^2$ are identical of different and each of them represents a hydrogen atom or an alkyl radical comprising 1 to 4 carbon atoms, or an alkenyl radical comprising 1 to 4 carbon atoms or an aryl radical.

2. The material according to claim 1, wherein the solid support (S) comprises a mineral oxide.

3. A material adapted for extracting metal cations in an aqueous medium, comprising polyazacycloalkane compounds (PACs) immobilized on a solid support (S), the material fitting the following formula (II):

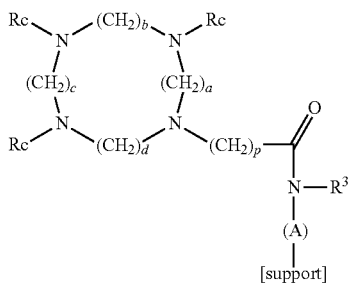

wherein:
- p=1, 2 or 3;
- $R^3$ represents a hydrogen atom, or an alkyl radical comprising 1 to 4 carbon atoms, or an alkenyl radical comprising 1 to 4 carbon atoms or an aryl radical; and
- -(A)- represents a saturated or unsaturated, linear or branched hydrocarbon chain, optionally interrupted by one or more heteroatoms, bound by at least one covalent bond to the solid support (S);
- a, b, c and d are three integers, either identical or different, each of a, b, c and d being equal to 2 or 3;
- each of the 3 Rc groups, either identical or different represents a group fitting the general formula:

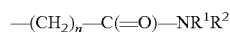

wherein n=1, 2 or 3; and
$R^1$ and $R^2$ are identical of different and each of them represents a hydrogen atom or an alkyl radical comprising 1 to 4 carbon atoms, or an alkenyl radical comprising 1 to 4 carbon atoms or an aryl radical.

4. The material according to claim 3, wherein the solid support (S) comprises a mineral oxide.

5. The material according to claim 3, comprising the polyazacycloalkane compounds (PACs) immobilized on the solid support (S), the material fitting the following formula (IIa):

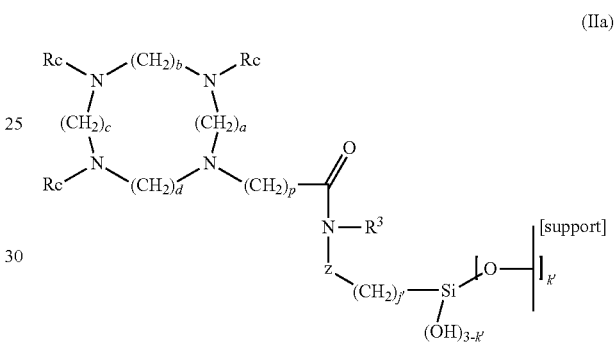

wherein:
- a, b, c, d, p and the groups Rc and $R^3$ have the meanings given in claim 3;
- z is a saturated or unsaturated, linear or branched divalent hydrocarbon group;
- j' is a integer equal to 0, 1, 2 or 3; and
- k', which represents the number of bonds between the cyclic species and the solid support (S), is an integer equal to 1, 2 or 3.

6. The material according to claim 5, wherein the solid support (S) comprises a mineral oxide.

7. A method for scavenging metal ions comprising contacting a liquid medium containing metal cations with the material as defined in claim 1.

8. A method for scavenging metal ions comprising contacting a liquid medium containing metal cations with the material as defined in claim 3.

9. A method for scavenging metal ions comprising contacting a liquid medium containing metal cations with the material as defined in claim 5.

10. A method for purifying a liquid medium contaminated with metal cations comprising contacting the liquid medium with a material as defined in claim 1.

11. The method according to claim 10, wherein the metal cations are $Pb^{2+}$ cations.

12. A method for purifying a liquid medium contaminated with metal cations comprising contacting the liquid medium with a material as defined in claim 3.

13. The method according to claim 12, wherein the metal cations are $Pb^{2+}$ cations.

14. A method for purifying a liquid medium contaminated with metal cations comprising contacting the liquid medium with a material as defined in claim 5.

15. The method according to claim 14, wherein the metal cations are $Pb^{2+}$ cations.

* * * * *